(12) United States Patent
Seul et al.

(10) Patent No.: US 7,118,900 B2
(45) Date of Patent: Oct. 10, 2006

(54) DIRECTED ASSEMBLY OF FUNCTIONAL HETEROSTRUCTURES

(75) Inventors: Michael Seul, Fanwood, NJ (US); Sukanta Banerjee, North Brunswick, NJ (US); Kairali Podual, North Brunswick, NJ (US); Ye Hong, Piscataway, NJ (US)

(73) Assignee: BioArray Solutions Ltd., Warren, NJ (US)

( * ) Notice: Subject to any disclaimer, the term of this patent is extended or adjusted under 35 U.S.C. 154(b) by 717 days.

(21) Appl. No.: 10/176,551

(22) Filed: Jun. 21, 2002

(65) Prior Publication Data

US 2003/0138842 A1    Jul. 24, 2003

Related U.S. Application Data

(63) Continuation-in-part of application No. 10/034,727, filed on Dec. 26, 2001.

(60) Provisional application No. 60/300,025, filed on Jun. 21, 2001, now abandoned.

(51) Int. Cl.
    *C12N 11/04*    (2006.01)
(52) U.S. Cl. ............... 435/182; 204/469; 204/470; 436/515; 436/535
(58) Field of Classification Search ........... 427/459, 427/201, 487, 198; 205/109, 221, 198, 158, 205/118; 204/477, 456; 435/182, 4, 7.1, 435/7.2, 6; 436/518, 56, 523–535
See application file for complete search history.

(56) References Cited

U.S. PATENT DOCUMENTS

| 4,383,529 | A | * | 5/1983 | Webster .............. 604/20 |
|---|---|---|---|---|
| 5,266,238 | A | | 11/1993 | Haacke et al. .......... 252/582 |
| 5,281,370 | A | | 1/1994 | Asher et al. .......... 264/1.1 |
| 5,552,270 | A | | 9/1996 | Khrapko et al. ........ 435/6 |
| 5,770,721 | A | | 6/1998 | Ershov et al. ......... 536/25.3 |
| 6,023,540 | A | * | 2/2000 | Walt et al. ............. 385/12 |
| 6,143,499 | A | | 11/2000 | Mirzabekov et al. ...... 435/6 |
| 6,251,691 | B1 | | 6/2001 | Seul |
| 6,730,515 | B1 | | 5/2004 | Kocher |
| 2002/0015952 | A1 | * | 2/2002 | Anderson et al. ........ 435/6 |

(Continued)

FOREIGN PATENT DOCUMENTS

WO    WO 97/40385 A1    10/1997

(Continued)

OTHER PUBLICATIONS

Lee et al., "Combination of Insulin-Like Growth Factor (IGF)-I and IGF-Binding Protein-1 Promotes Fibroblast-Embedded Collagen Gel Contraction" (1996) Endocrinology 137:5278-5283.*

(Continued)

*Primary Examiner*—Long V. Le
*Assistant Examiner*—Christine Foster
(74) *Attorney, Agent, or Firm*—Eric P. Mirabel; Daniel A. Monaco

(57) ABSTRACT

The present invention relates to a systematic process for the creation of functionally organized, spatially patterned assemblies of polymer-microparticle composites including the AC electric field-mediated assembly of patterned, self-supporting organic (polymeric) films and organic-polymer-microparticle composites of tailored composition and morphology. The present invention further relates to the incorporation of said assemblies into other structures. The present invention also relates to the application of such functional assemblies in materials science and biology. Additional areas of application include sensors, catalysts, membranes, and micro-reactors, and miniaturized format for generation of multifunctional thin films. This invention also provides simple methods and apparatus for synthesizing thin films of tailored composition and morphology.

16 Claims, 23 Drawing Sheets

U.S. PATENT DOCUMENTS

| | | | |
|---|---|---|---|
| 2002/0031841 A1* | 3/2002 | Asher et al. | 436/518 |
| 2002/0166766 A1 | 11/2002 | Seul et al. | |
| 2003/0006143 A1* | 1/2003 | Banerjee et al. | 205/414 |
| 2003/0082587 A1 | 5/2003 | Seul et al. | |
| 2003/0228610 A1* | 12/2003 | Seul | 435/6 |
| 2004/0048259 A1* | 3/2004 | Hashmi et al. | 435/6 |
| 2004/0229269 A1* | 11/2004 | Hashmi et al. | 435/6 |

FOREIGN PATENT DOCUMENTS

| | | |
|---|---|---|
| WO | WO 01/98765 A1 | 12/2001 |

OTHER PUBLICATIONS

Matthews et al. "Biochemistry: A Short Course," New York: John Wiley & Sons, Inc (1997), p. 25.*

Cruse et al., "Illustrated Dictionary of Immunology," Boca Raton: CRC Press (2003) p. 512.*

Proudnikov, D. et al, "Immobilization of DNA in Polyacrylamide Gel for the Manufacture of DNA and DNA-Oligonucleotide Microchips", Analytical Biochemistry, vol. 259, pp. 34-41 (1998).

Chen, G. et al., "pH-Sensitive Thin Hydrogel Microfabricated by Photolithography", Langmuir, vol. 14, pp. 6610-6612 (1998).

Gelfi, C. et al. "Investigation of the Properties of Novel Acrylamido Monomers by Capilary Zone Electrophoresis", Journal of Chromatography, vol. 608, pp. 333-341 (1992).

Warren, J. A. "Selected Spacings During Directional Solidification of a Binary Alloy", Spatio-Temporal Patterns, Ed. P.E. Cladis and P. Palffy-Muhoray, SFI Studies in the Science of Complexity, Addison-Wesley, pp. 91-105 (1995).

Ito., Y. et al "Patterned Immobilization of Thermoresponsive Polymer", Langmuir, vol. 13, pp. 2756-2759, (1997).

Otero, T. F. et al. "Electrochemically initiated acrylic acid/ acrylamide copolymerization", J. Electroanal. Chem., vol. 256, pp. 433-439. (1988).

Beebe, D. J. et al. "Functional hydrogel structures for autonomous flow control inside microfluidic channels", Nature, vol. 404, pp. 588-590 (2000).

Liang, L. et al. "Preparation of Composite-Crosslinked Poly(N-isopropylacrylamide) Gel Layer and Characteristics of Reverse Hydrophilic-Hydrophobic Surface", Journal of Applied Polymer Science, vol. 72, pp. 1-11, (1999).

Kim E., et al. "Polymer microstructures formed by moulding in capillaries", Nature, vol. 376, pp. 581-584, (1995).

Otero T. F., et al. "Electroinitiated polymerization of acrylamide in DMF: Attempts at an interfacial model", J. Electroanal. Chem., vol. 304, pp. 153-170, (1991).

Righetti, P. G. et al., "Electrophoresis gel media: the state of the art", Journal of Chromatography B, vol. 699, pp. 63-75 (1996).

Tanaka T. et al., "Mechanical Instability of gels at the phase transition", Nature, vol. 325, pp. 796-798, (1987).

L. Liang et al. "Temperature-sensitive membranes prepared by UV photopolymerization of N-isopropylacrylamide on a surface of porous hydrophilic polypropylene membranes", Journal of Membrane Science, vol. 162, pp. 235-246 (1999).

Holtz, J., et al., "Intelligent Polymerized Crystalline Colloidal Arrays: Novel Sensor Materials", Analytical Chemistry, vol. 70, No. 4, pp. 780-791, (1998).

Kumacheva, E. et al., "Three-dimensional Arrays in Polymer Nanocomposites", Advanced Materials, vol. 11, No. 3, pp. 231-234, (1999).

K Vorlop, K.-D., et al., "Entrapment of Microbial Cells Within Polyurethane Hydrogel Beads with the Advantage of Low Toxicity", Biotechnology Techniques, vol. 6, No. 6, pp. 483-488, (1992).

LaForge, K. S. et al., "Detection of Single Nucleotide Polymorphisms of the Human Mu Opioid Receptor Gene by Hybridization of Single Nucleotide Extension on Custom Oligonucleotide Gelpad Microchips:Potential in Studies of Addiction", American Journal of Medical Genetics (Neuropsychiatric Genetics) vol. 96, pp. 604-615, (2000).

Yershov G., et al., "DNA analysis and diagnostics on oligonucleotide microchips", Proceedings of the National Academy of Sciences USA, vol. 93, pp. 4913-4918 (1996).

Kalinina O. et al., "A 'Core-Shell' Approach to Producing 3D Polymer Nanocomposites", Macromolecules, vol. 32, pp. 4122-4129, (1999).

Jackman, R. J. et al., "Using Elastomeric Membranes as Dry Resists and for Dry Lift-Off", Langmuir vol. 15, pp. 2973-2984 (1999).

Jeon, N. L. et al, "Patterned polymer growth on silicon surfaces usiing microcontact printing and surface-initiated polymerization", Applied Physics Letters, vol. 75, No. 26, pp. 4201-4203 (1999).

Y. Iwayama, et al. "Optically Tunable Gelled Photonic Crystal Covering Almost the Entire Visible Light Wavelength Region." Langmuir, vol. 19(4):977-980, 2003.

S.R. Dziennik, et al. "Nondiffusive mechanisms enhance protein uptake rates in ion exchange particles." PNAS, 2003: 420-425. vol. 100, No. 2.

A. Hatch, et al. "Diffusion Immunoassay in Polyacrylamide Hydrogels." Micro Total Analysis Systems, 2001: 571 572.

N. Fatin-Rouge, et al. "Diffusion and Partitioning of Solutes in Agarose Hydrogels: The Relative Influence of Electrostatic and Specific Interactions". J. Phys. Chem. B., 2003: 12126-12137. vol. 107.

P. Krsko et al. "Electron-Beam Surface-Patterned Poly(ethylene glycol) Microhydrogels", Langmuir, 2003: 5618-5625. vol. 19.

P. Ghosh, et al. "A Simple Lithographic Approach for Preparing Patterned. Micron-Scale Corrals for Controlling Cell Growth." Angew. Chem. Int. Ed., 1999: 1592-1595. vol. 38, No. 11.

W-G. Koh, et al. "Poly(ethylene glycol) Hydrogel Microstructures Encapsulating Living Cells," Langmuir, 2002: 2459-2462. vol. 18.

W-G. Koh, et al. "Molding of Hydrogel Microstructures to Create Multiphenotype Cell Microarrays." Analytical Chemistry, 2003.

C. Bandeira-Melo et al. "EliCell: a gel-phase dual antibody capture and detection assay to measure cytokine release from eosinophils," Journal of Immunological Methods, 2000: 105-115, vol. 244.

One Cell Systems Product Information, http://www.onecell.com/AboutUs.htm.

Sentek Group, Inc. Product Information. http://www.sentekgroup.com/glucoview.htm.

* cited by examiner (a)

(b)

Flip gel with exposed microparticles

Assay Format

Assay result

DIRECTED ASSEMBLY OF FUNCTIONAL HETEROSTRUCTURES

CROSS-REFERENCE TO RELATED APPLICATION

This application is a Continuation-in-Part of non-provisional U.S. application Ser. No. 10/034,727 filed Dec. 26, 2001. This application claims priority to non-provisional U.S. application Ser. No. 10/032,727 and U.S. Provisional Application No. 60/300,025, filed Jun. 21, 2001, now abandoned both of which are incorporated herein by reference in their entirety.

BACKGROUND OF THE INVENTION

A longstanding objective within the materials, engineering, biomedical and analytical sciences has been the design of ever-smaller structures and devices for use in miniature systems capable of performing specific functions, such, as sensors, transducers, signal processors or computers. Of particular interest as potential building blocks in this context have been functional materials having predetermined properties. Patterned films composed of suitable polymers and polymer-microparticle composites offer particularly attractive opportunities to realize hierarchically organized structures of functional materials and to provide confinement and segregation for performing "local" chemical reactions.

Several methods of preparing patterned polymer films and polymer-microparticle composites have been described. In one example, polymer molding has been used to prepare polymeric films. Beginning with a master that is fabricated from a silicon (Si) wafer using conventional lithographic techniques, a mold is made using an elastomer such as polydimethylsiloxane (PDMS). The mold is then used to produce replicas in a UV-curable polymer such as polyurethane. The applicability of this technique of polymer molding, long used for replication of micron-sized structures in devices such as diffraction gratings, compact disks, etc., recently has been extended to nanoscale replication (Xia, Y. et al., Adv. Mater. 9: 147 (1997), Jackman, R. J. et al., Langmuir. 15:2973 (1999), Kim, E. et al. Nature 376, 581 (1999).

Photolithography has been used to produce patterned, stimuli-sensitive polymeric films which can be further functionalized with bioactive molecules and which undergo abrupt changes in volume in response to changes in pH and temperature (Chen, G. et al., Langmuir. 14:6610 (1998); Ito, Y. et al., Langmuir 13: 2756 (1997)). UV-induced patterned polymerization of various hydrogel structures within microchannels has been described as a means for the autonomous control of local flow (Beebe, D. J. et al., Nature. 404:588 (2000)).

Surface-initiated ring-opening metathesis polymerization following microcontact printing has been used to create patterned polymer layers which remain attached to the surface and produce structures of controlled vertical and lateral dimensions (Jeon, N. L. et al., Appl. Phys. Lett. 75:4201 (1999)). Other techniques such as thermal radical polymerization (Liang, L., J. Appl. Polym. Sci. 72:1, (1999)) and UV-induced polymerization (Liang, L., J. Membr. Sci. 162:235 (1999)) have been used to generate surface-confined, thin, uniform and stimuli-sensitive polymeric films.

Sarasola, J. M. et al. (J. Electroanal. Chem. 256:433, (1988)) and Otero, T. F. et al. (J. Electroanal. Chem. 304: 153, (1991)) describe electropolymerization of acrylamide gels using a Faradaic process. Acrylamide gels are prepared on electrode surfaces by an anodic oxidative polymerization process using the electroactive nature of acrylamide monomers.

Polymerization of crosslinked acrylamide has been reported to produce a matrix of glass-immobilized polyacrylamide pads which were activated with receptor molecules of interest including oligonucleotides or proteins. The use of the resulting porous and highly hydrated matrix for simultaneous monitoring of ligand-receptor binding reactions has been reported (Proudnikov, D. et al., Anal. Biochem. 259:34 (1998); Yershov, G., Proc. Natl. Acad. Sci. U.S.A. 93:4913 (1996), LaForge, S. K., Am. J. Med. Genet. 96:604 (2000); Khrapko, K. R. et al. U.S. Pat. No. 5,552,270, 1996; Ershov,G. M. et al. U.S. Pat. No. 5,770,721, 1998; Mirzabekov et al. U.S. Pat. No. 6,143,499). It should be noted, however, that a potential drawback of the methodology used in these studies is that forming the gel-matrix for the assay is labor-intensive and difficult, especially if a densely packed matrix is desired. Additionally, when the gel-pads of the matrix have sizes on the length scale of microns, it is a considerable technological challenge to deliver the bioactive molecules reproducibly and reliably to each gel-pad in the array.

A process for the assembly of a 3-D array of particles has been reported which is based on the synthesis of a core-shell latex particle containing a core polymer with a glass transition temperature significantly higher than that of the shell polymer. In accordance with that process, particles were assembled into a 3-D close packed structure and annealed in such a way that the core particle remained unaltered while the shell polymer flowed, resulting in a continuous matrix embedding an organized 3-D array of core particles (Kalining, O. and Kumacheva, E., Macromolecules. 32:4122 (1999); Kumacheva, E. et al., Adv. Mater. 11:231 (1999), Kumacheva, E. et al., U.S. Pat. No. 5,592,131 (1999)). However, the reported assembly of the 3D array is quite slow because it relies on particle sedimentation. Second, because the outer shells of the particles are destroyed as a result of annealing, the particles cannot be reused.

The encapsulation of a colloidal crystalline array within a thin, environmentally sensitive hydrogel matrix capable of swelling in response to changes in pH and temperature has also been reported. In other instances, the hydrogel contained immobilized moieties capable of triggering the swelling of the gel in the presence of particular analytes. The swelling of the gel matrix increases the periodicity of the colloidal crystal array and produces a shift in Bragg diffraction peaks in the spectra of the scattered light (Holtz, J. H. et al., Anal. Chem. 70:780 (1998); Hacke, G. et al., U.S. Pat. No. 5,266,238, 1993; Asher, S. A., U.S. Pat. No. 5,281,370, 1994). In most of these references, the process of forming a colloid crystal relies on passive diffusive transport of particles within the prepolymer reactive mixture, which tends to be slow. In one reference, however, a process was reported in which an electric field was applied to a colloid suspension to increase the rate of formation of a colloid crystal. It should be noted that, regardless of whether an electric field is used, the processes reported in these references only produce a simple colloid crystal. More sophisticated colloid crystal structures, such as patterned two-dimensional colloid crystals, are not readily produced by these methods.

Each of the aforementioned references are incorporated herein by reference in its entirety

SUMMARY OF THE INVENTION

One aspect of this invention is to provide a method of forming a patterned polymeric film. In this method, a first electrode is positioned in a first plane and a second electrode is positioned in a second plane that is different from the first plane. A polymerization mixture comprising a monomer and an initiator in an electrolyte solution is added to the space between the first and the second electrode. An AC electric field is generated at an interface between the first electrode and the electrolyte solution. Here, the first electrode may be a light-sensitive electrode. If so, the method further comprises the step of illuminating the first electrode with a predetermined light pattern, such that the illumination, in combination with the AC field generated at the interface between the first electrode and the electrolyte solution, results in the formation of a patterned film in a designated area on the first electrode. The designated area is defined by the illumination pattern. Alternately, the first electrode can be an electrode with a surface and an interior. In this case, the surface or interior (or both) is/are modified to produce spatial modulations in certain properties of the first electrode, particularly properties that affect the local distribution of the electric field at the interface between the electrode and the electrolyte solution. As a result, the generation of an AC electric field at the interface results in the formation of the patterned film in a designated area of the first electrode. In this second case, the designated area is defined by spatial modulations in the properties of the first electrode.

Another aspect of this invention is to provide a method of forming an assembly of particles embedded in a polymeric film. In this method, a first electrode and a second electrode are provided. A polymerization mixture comprising a monomer and an initiator in an electrolyte solution also containing a plurality of suspended particles is added to the region between the first and the second electrode. An AC electric field is generated at an interface between the first electrode and the electrolyte solution. When the first electrode is a light-sensitive electrode, the method further comprises the step of illuminating the first electrode with a predetermined light pattern, such that the illumination, in combination with the AC field generated at the interface between the first electrode and the electrolyte solution, results in the formation of an assembly of particles in a designated area corresponding to the predetermined light pattern on the first electrode. The designated area is defined by the illumination pattern. Alternately, the first electrode can be an electrode with a surface and an interior. In this case, the surface or interior (or both) is/are modified to produce spatial modulations in certain properties of the first electrode, particularly properties that affect the local distribution of the electric field at the interface between the electrode and the electrolyte solution. As a result, the generation of an AC electric field at the interface results in the formation of the assembly of particles in a designated area of the first electrode. In this second case, the designated area is defined by spatial modulations in the properties of the first electrode. After the particle assemblies are formed, the polymerization mixture is polymerized to form a polymer-particle composite, which has an assembly of particles embedded in the polymer.

In another aspect of this invention, a method of detecting a binding interaction between a biomolecule and a target compound is provided. This method comprises providing an assembly of beads embedded in a hydrophilic polymeric matrix. The beads have biomolecules attached to their surfaces. Subpopulations of beads are provided, wherein each bead of a given subpopulation can be distinguished by the type of biomolecule attached to it, as well as by a unique chemical or physical characteristic that identifies the bead type. The beads are placed in contact with a target compound so as to allow a target compound to bind to the corresponding biomolecule to form a target-biomolecule complex. The target-biomolecule complex is then detected. The biomolecule of the target-biomolecule complex is then identified by means of the unique chemical or physical characteristic of the type of bead associated with the complex.

Yet another aspect of this invention is to provide a method of forming an assembly of particles embedded in a gel. This method comprises the step of providing a first electrode and a second electrode. An electrolyte solution containing a gellable component and a plurality of suspended particles is added to the region between the first and second electrode. The formation of gels by suitable gellable components is preferably temperature dependent. An AC electric field is generated at an interface between the first electrode and the electrolyte solution. When the first electrode is a light-sensitive electrode, the method further comprises the step of illuminating the first electrode with a predetermined light pattern, such that the illumination, in combination with the AC field generated at the interface, results in the formation of an assembly of particles in a designated area of the first electrode. The designated area in this case is defined by the illumination pattern. Alternately, the first electrode can be an electrode having a surface and an interior. In this case, the surface and/or interior of the electrode is/are modified to produce spatial modulations in certain properties of the first electrode, particularly properties affecting the local distribution of the electric field at the interface. Generation of an AC electric field at the interface results in the formation of an assembly of particles in a designated area of the first electrode. The designated area is defined by the spatial modulations in the properties of the first electrode. After an assembly of particles is formed, the temperature of the gellable component is decreased while maintaining the AC field, in order to form a polymer-particle composite gel. The composite gel obtained in this way comprises an assembly of particles embedded in a gel.

This invention also provides a polymer-bead composite. The composite comprises a assembly of beads embedded in a hydrophilic polymeric matrix. The beads have biomolecules attached to their surfaces, and each type of bead can be distinguished by the biomolecules attached to it. Each type of bead is further distinguishable by a unique chemical or physical characteristics that identifies the bead type.

Another aspect of this invention is to provide a method of sorting one population of particles from another. This method involves providing a cell that comprises a first electrode positioned in a first plane and a second electrode positioned in a second plane different from the first plane. A polymerization mixture containing a monomer and an initiator in an electrolyte solution is added to the region between the first and the second electrode. The electrolyte solution also contains a plurality of particles suspended in the solution. The particles comprise a mixture of at least two populations of particles having different relaxation frequencies. An AC electric field is applied to an interface between the first electrode and the electrolyte solution. The frequency of the AC field is selected such that an array composed of particles having relaxation frequencies exceeding the frequency of the applied field are selectively assembled. The particles having relaxation frequencies less than said applied frequency are not assembled. When the first electrode of this method is a light-sensitive electrode, the method further comprises the step of illuminating the first electrode with a predetermined light pattern, such that the illumination, in combination with the AC field generated at the interface, results in the formation of an assembly of particles in a designated area of the first electrode. The designated area in this case is defined by the illumination pattern. Alternately, the first electrode may be an electrode having a surface and an interior. In this case, the surface and/or interior of the electrode is/are modified to produce spatial modulations in certain properties of the first electrode, particularly properties affecting the local distribution of the electric field at the interface. Generation of an AC electric field at the interface results in the formation of an assembly of particles in a designated area of the first electrode. The designated area is defined by the spatial modulations in the properties of the first electrode. After the assembly of particles is formed, the polymerization mixture is polymerized to form a polymer-particle composite. The composite formed in this manner comprises an array of particles embedded in the polymer. Particles that are not assembled in the array are removed from the cell, either before or after the polymerization step.

Yet another aspect of this invention is to provide a method of sorting one population of particles from another. This method comprises the step of: providing a first electrode positioned in a first plane and a second electrode positioned in a second plane different from the first plane. An electrolyte solution containing a gellable component and a plurality of suspended particles is added to the region between the two electrodes. The formation of gels by gellable components suitable for this invention is either temperature dependent or activated by light. The plurality of particles comprises a mixture of at least two populations of particles having different relaxation frequencies. An AC electric field is applied at an interface between the first electrode and said electrolyte solution. The frequency of the AC field is selected such that an array composed of particles having relaxation frequencies exceeding the frequency of the applied field is selectively assembled. Particles having relaxation frequencies less than the applied frequency are not assembled. When the first electrode is a light-sensitive electrode, the method further comprises the step of illuminating the first electrode with a predetermined light pattern, such that the illumination, in combination with the AC field generated at the interface, results in the formation of an assembly of particles in a designated area of the first electrode. The designated area in this case is defined by the illumination pattern. Alternately, the first electrode is an electrode having a surface and an interior. In this case, the surface or interior of the electrode is modified to produce spatial modulations in certain properties of the first electrode, particularly properties affecting the local distribution of the electric field at the interface. Generation of an AC electric field at the interface results in the formation of an assembly of particles in a designated area of the first electrode. The designated area is defined by the spatial modulations in the properties of the first electrode. After a particle array is formed, particles that are not part of the array are removed. The gel is then formed. If temperature dependent gellable components are used, the temperature of the gellable component is decreased while maintaining the AC field to form a polymer-particle composite gel. Alternately, if photoactivated gellable components are used, the composite gel can be formed by irradiation with light. The composite gel formed by this method comprises an assembly of particles embedded in gel.

Yet another aspect of this invention is to provide a method of producing an organized assembly by transforming a homogeneous fluid mixture or suspension comprising a gellable component and a plurality of particles within a reactor, into one or more heterogeneous assemblies. The method comprises the following steps: (a) actively forming a spatial arrangement of a plurality of particles in designated regions of one or more bounding surfaces of the reactor. Here, the active formation is mediated by an external field and sustained in the arrangement after the formation by the field; (b) forming a gel in the presence of the external field, in order to form a gel-particle composite. In another aspect of this invention, a method of performing an assay is provided. This method comprises the step of providing a first electrode and a second electrode. A polymerization mixture comprising a monomer and an initiator in an electrolyte solution also containing a plurality of suspended particles is added to the region between the first and the second electrode. The particles comprise subpopulations of particles, with each subpopulation being distinguishable by the type of binding agent attached to the surface. The particles also have a chemically or physically distinguishable characteristic. An AC electric field is generated at an interface between the first electrode and the electrolyte solution. When the first electrode is a light-sensitive electrode, the method further comprises the step of illuminating the first electrode with a predetermined light pattern, such that the illumination, in combination with the AC field generated at the interface between the first electrode and the electrolyte solution, results in the formation of an assembly of particles in a designated area corresponding to the predetermined light pattern on the first electrode. The designated area is defined by the illumination pattern. Alternately, the first electrode can be an electrode with a surface and an interior. In this case, the surface or interior (or both) is/are modified to produce spatial modulations in certain properties of the first electrode, particularly properties that affect the local distribution of the electric field at the interface between the electrode and the electrolyte solution. As a result, the generation of an AC electric field at the interface results in the formation of the assembly of particles in a designated area of the first electrode. In this second case, the designated area is defined by spatial modulations in the properties of the first electrode. After the particle assemblies are formed, the polymerization mixture is polymerized to form a polymer-particle composite, which has an assembly of particles embedded in the polymer. In some embodiments of this invention, at least one electrode is then removed to expose the particles embedded in the polymer. The exposed particles are placed in contact with a solution containing at least one target analyte and the binding reaction between the binding agent and the target analyte is detected. In other embodiments of this invention, the polymer-particle composite is exposed to a target analyte while it is still sandwiched between the two electrodes.

The present invention provides methods for synthesizing patterned polymeric films and polymer-microparticle composites. The methods are simple to implement and flexible because they are compatible with a variety of polymer chemistries. Also provided is an apparatus useful for making the patterned polymer films and polymer-microparticle composites. Patterned polymer films and polymer-microparticle composites and their uses are also provided.

DETAILED DESCRIPTION OF THE INVENTION

Figure 1:
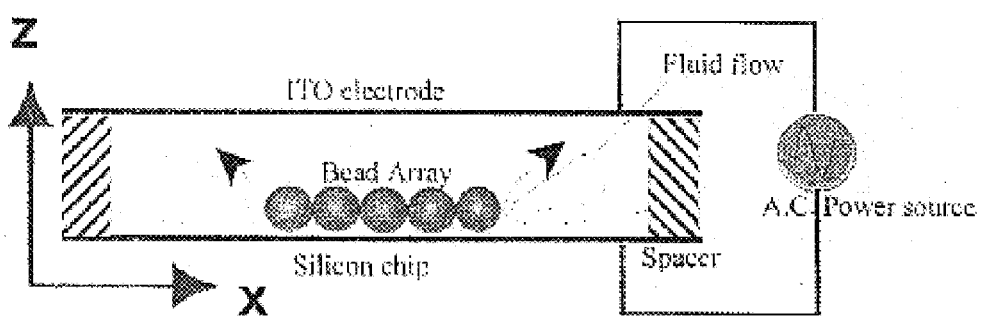
FIG. 1 is an illustration showing an experimental configuration for LEAPS.

Patterned polymeric films and polymer-microparticle composites are useful in many areas of technology, including biology, electronics, optoelectronics, and materials science. This invention provides methods for manufacturing such patterned films and polymer-microparticle composites, as well as the pattern films and composites themselves. One advantage of this invention is that it provides a rapid method of forming an ordered polymer-microparticle composite that is suitable for use in biological assays. Another advantage is that the formation of the polymer-microparticle composites is even reversible under certain conditions, such that the composite can be disassembled at will to recover the microparticles after a biological assay is completed. Further, in contrast to gel array based assays reported earlier, the methods of forming the polymer-microparticle composites of this invention are very simple, which make the composites attractive for large-scale, multiplexed assays.

Certain embodiments of this invention make use of the methods collectively known as "LEAPS" ("Light-Controlled Electrokinetic Assembly of Particles near Surfaces" as described in U.S. Pat. No. 6,251,691, hereby incorporated by reference). In these embodiments, LEAPS is used to direct the self-assembly of microparticles to form arrays in designated positions on a planar or substantially planar substrate. In using LEAPS in accordance with the methods, of this invention, it is possible to form one or more microparticle arrays on a substrate. When a plurality of microparticle arrays is desired, the arrays may be formed simultaneously or sequentially on the substrate. Sequential formation of a plurality of arrays is possible because LEAPS can be used to spatially confine microparticle arrays that are already formed. The use of LEAPS in combination with externally triggered, template-directed gel chemistries provides heterostructures that are organized in accordance with user-defined architecture designed to meet the requirements associated with the execution of specific functions. Applications of the process to the fabrication of functional materials, sensors and more generally chemical transducers and information processors also are of interest.

Formation of Patterned Polymeric Film

The present invention provides methods for forming patterned polymeric film using LEAPS. In certain embodiments of this invention, a polymerization mixture is provided comprising a monomer and an initiator in an electrolyte solution. Preferably, the polymerization mixture also contains a cross-linker, with the monomer, initiator and the crosslinker dissolved in the electrolyte solution. When LEAPS is used to pattern the polymeric films, this mixture is placed between a first electrode (e.g., silicon), which may be light sensitive and/or patterned and a second electrode (e.g., indium-tin-oxide (ITO)) that is parallel to the first. An AC electric field is generated at the interface between the electrolyte solution and the first electrode. Lateral impedance gradients at the interface, set up by the patterning or illumination, give rise to local recirculating electro-osmotic fluid motion, which effectively transports fluid (and particles if they are present) from regions of high impedance to regions of low impedance. Depending on the initiators used, the application of the AC electric field, in addition to the illumination of the first (when a light-sensitive electrode is used) or the patterning of the electrode (when a patterned electrode is used), induces formation of a patterned polymeric film on the low impedance regions of the electrode.

In preferred embodiments, the polymerization is triggered at a desired time by using initiators that are heat or photo-activated. Such heat or photoactivated triggering occurs when heat-generated or UV-generated free radicals diffuse and react with monomers to produce initially oligomers and finally a crosslinked polymer film.

As the gel film grows, a moving reaction extends into the solution with time. In case of the heat-induced polymerization, polymerization starts from the first electrode. Due to the presence of LEAPS-mediated, strong convective transport near the first electrode surface, the polymerization process is triggered preferentially in the low impedance areas on the first electrode, thereby giving rise to a spatially patterned polymeric film on said electrode. In case of UV-induced polymerization, however, polymerization starts at the second electrode and produces an unpatterned monolithic gel.

Gels of the present invention may have a wide range of porosity and include non-porous, microporous and macroporous gels. It is to be understood that non-porous gels refer to gels with a microscopic structure such that the space between the macromolecular chains is the main area for diffusion. Generally, non-porous gels do not have a network of pores and any pores that are present have a pore size less than 5 nm. It is to be understood that microporous gels refer to gels which have a porous structure with pore sizes ranging from about 5 to about 50 nm. It is to be understood that macroporous gels refer to gels which have a porous structure with a pore size greater than 50 nm. Furthermore, depending on the polymer components, the degree of porosity and size of "pores" is based on the density of the lattice or matrix formed by the crosslinking of polymer strands.

Figure 6:
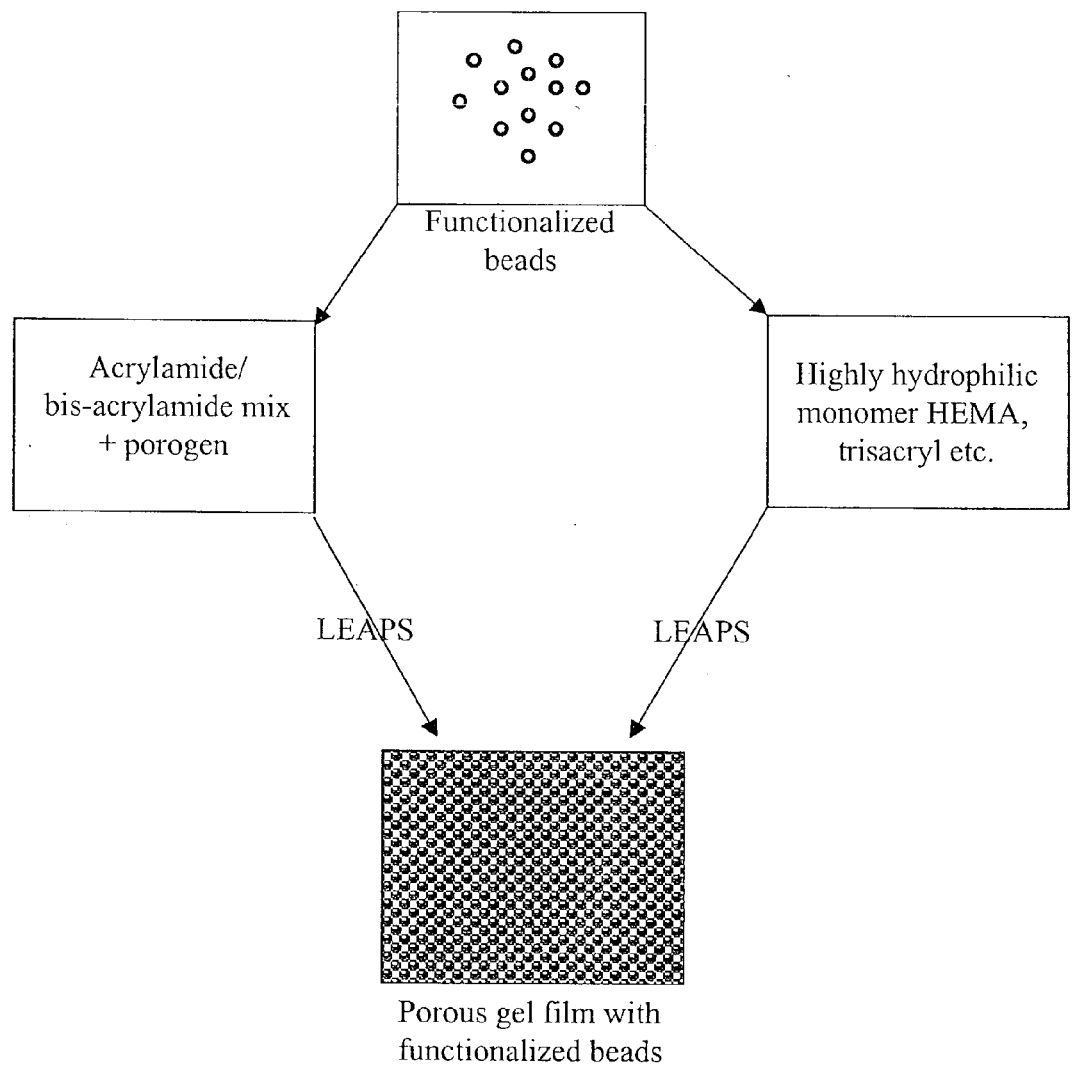
FIG. 6 is an illustration showing two exemplary processes for produce porous a gel-particle composite.

Non-limiting examples of useful gels are polyacrylamide gels, which can have pore sizes ranging from a few nm to also 15 to 20 nm in highly diluted formulations. To facilitate the penetration of large DNA fragments and other molecules into gels, macroporous polyacrylamides may be prepared by polymerizing in the presence of preformed polymers such as poly(ethylene glycol)(PEG), polyvinyl pyrrolidone (PVP), hydroxymethyl cellulose (HMC) etc. (Righetti, P. G. and Gelfi, C. 1996. J. Chromatogr. B. 699: 63–75). Highly hydrophilic monomers, such as trisacryl may also be used to produce highly porous gels (Gelfi, C., et al. 1992. J. Chromatogr. 608: 333–341). FIG. 6 illustrates the protocol to form a porous gel using preformed polymers.

The present invention, in contrast to several known methods, does not require complex implementation, such as use of a mask, in preparation of patterned gel films. In addition, the methods of the present invention allow increased flexibility in choice of monomers, crosslinkers and initiators used. It should, however, be noted that high viscosity of the polymerization mixture and high ionic concentration may impede with the proper functioning of LEAPS by interfering with the interfacial fluid flow. Accordingly, it is recommended that the ionic concentration of the polymerization mixture be about 1.0 mM or lower, preferably between about 0.01 mM to 0.1 mM. This may be accomplished by selecting initiators to maintain low ionic concentration of the mixture. Initiators, like monomers and crosslinkers, are well known in the art and may readily be obtained from commercial sources.

Two types of initiators are preferably used with this invention, namely thermal initiators and photoinitiators. Non-limiting examples of thermal initiators include VA-044 (2,2'-Azobis (N,N' dimethyleneisobutyramidine) dihydrochloride, V-50 (2,2'-Azobis(2-amidinopropane) dihydrochloride, VA-061 (2,2'-Azobis (N, N'dimethyleneisobutyramidine), V-501 (4,4'-Azobis (4-cyanopentanoic acid), VA-086 (2,2'Azobis[2-methyl-N-(2-hydroxyethyl) propionamide). Non-limiting examples of photoinitiators include Ciba IRGACURE 2959 (1-[4-(2-Hydroxyethoxy)-phenyl]-2-hydroxy-2-methyl-1-propane-1-one), (Ciba Specialty Chemicals Inc.), DEAP (Diethoxyacetophenone) (Acros Organics), Ciba DAROCUR 1173 (2-Hydroxy-2-methyl-1-phenyl-propan-1-one), (Ciba Specialty Chemicals Inc.), Ciba DAROCUR BP (Banzophenone), (Ciba Specialty Chemicals Inc.). As for the monomers and crosslinkers, it is recommended that low viscosity monomers and crosslinkers be used, such that the viscosity of the polymerization mixture is about 100 cp or less, more preferably 10 cp or less. Examples of monomers useful for this invention include those that are water soluble, with non-limiting examples including acrylamide, ethylene glycol acrylate, hydroxyethylacrylate, and acrylic acid. Other suitable monomers are not water soluble, but are still useful provided that a polarizable liquid medium is also used, as described below. Crosslinkers that are useful for this invention include those that are water soluble. Non-limiting examples include methylene-bis-acrylamide, PEG diacrylates, and ethyleneglycol diacrylate. Crosslinkers that are not water soluble may also be used as well, provided that a polarizable liquid medium is used in conjunction.

When the patterned film to be produced is a hydrogel, water-soluble monomers are preferred. In addition, when said film is optically transparent, the desired monomer concentration may be adjusted according to the type of gel to be produced (e.g., self-supporting or cleaved gel). In one embodiment, a mixture of acrylamide and bisacrylamide of varying monomer concentrations, from about 20% to about 3%. (acrylamide:bisacrylamide=37.5:1, molar ratio) may be used to produce a hydrogel. In preferred embodiments, the polymeric film obtained comprises a cross-linked alkylacrylamide or hydroxyalkylmethacrylate hydrogel.

The AC voltage depends on the polymerization mixture and is readily adjusted until the desired polymeric film (or polymer-microparticle composite) is formed. Preferably, the voltage applied is in the range of about 0.5 to about 15 $V_{p-p}$ (peak-to-peak voltage) and the frequency is preferably more than about 10 Hz and less than about 500 kHz, more preferably about 1 kHz to 10 kHz.

In one embodiment of the invention, LEAPS is carried out in a fluidic microcell formed by sandwiching a spacer between the first and second electrode. LEAPS and polymerization is then conducted as described above. In preferred embodiments of the present invention, an electrolyte solution (more preferably, an aqueous solution) is used in the polymerization mixture, e.g., to dissolve monomers, crosslinkers and initiators. In certain embodiments, other polarizable liquid media may be used, including non-aqueous solutions. In using a non-aqueous solution (e.g., DMSO and acetonitrile), an environment-dependent characteristic frequency of the particles known as the "relaxation" "frequency" is shifted to lower values than what would be observed in an aqueous solution. Among other things, the relaxation frequency of the particles is a measure of the particles' ability to move in response to time-varying electric fields.

The hydrogels of the present invention may be functionalized by a variety of methods known in the art. For example, during the polymerization step itself small amounts of functional monomers may be introduced along with the polymerization mixture (e.g., acrylamide mixture). Acrylic acid, 2-hydroxyethymethacrylate (HEMA), diethylaminoethylmethacrylate hydrochloride etc. may be incorporated into the hydrogel so that the micropatterned gel may be chemically addressed via the carboxy, hydroxy and amino functional groups. Biomolecules of interest may subsequently be immobilized in the gel using suitable chemistry and linker molecules.

Small probe molecules or functional co-monomers may also be introduced into the hydrogel using the same approach to yield novel sensor and stimuli-responsive hydrogel structures that can respond to a variety of inputs such a pH, temperature, electric field, light etc. Microscale structures made from such stimuli-responsive materials may act as an actuator, for example for controlling fluid flow (valve). Such structures are be self-regulating and would not require an external power source.

Polymer-Microparticle Composites

By providing a plurality of particles suspended in the polymerization mixture, the methods for patterned polymeric film synthesis, as described in the preceding section, may be used to obtain an assembly of the particles embedded in a polymeric film (also referred to as a "polymer-microparticle composite" or a "heterostructure"). The term "particle" as used herein includes, but is not limited to, colloidal particles (e.g., silica, modified polystyrene or other polymers), microspheres, eukaryotic and prokaryotic cells, micelles, vesicles (e.g., liposomes) and emulsion droplets. In preferred embodiment, the size of the particles range from about 0.2 to about 20 µm in diameter.

The formation of the polymer-microparticle composite is comprised of two stages. First, particle assemblies (e.g., planar particle assemblies, more preferably particle arrays) are formed from a particle suspension that also contains all of the ingredients required for subsequent in-situ gel formation, as described previously. In these embodiments, LEAPS may be used to form the particle assemblies. Alternately, other methods may be used as well. For example, if magnetic particles are used, a magnetic field may be used to induce particle array formation. The second stage of composite formation comprises the formation of a polymeric film formed to produce the polymer-microparticle composite. In one preferred embodiment, gels are formed by heat-initiated in-situ polymerization to form a composite in which the gels are spatially patterned. In another preferred embodiment, the gels are formed by UV-initiated in-situ polymerization to obtain a composite in which the gels are monolithic (not patterned).

For a given particle size, the voltage and frequency can be selected such that the transport of the fluid and particle is achieved from a high impedance to a low impedance region on the chip. By way of example, for a particle size of 2 microns, a voltage of from about 0.5 to about 20 V (AC peak-to-peak) and a frequency of from about 100 Hz to about 3 kHz can be applied to achieve particle/fluid transport. For a particle size of 5 microns, a voltage of from about 0.5 to about 20 V (AC peak-to-peak) and a frequency from about 100 Hz to about 1 kHz can be applied. For a particle size of 10 microns, a voltage of from about 0.5 to about 20 V (AC, peak-to-peak) and a frequency of from about 50 Hz to about 200 Hz can be applied. Fluid and particle transport and assembly may be monitored by video microscopy permitting frame capture and digitization of frames for further analysis.

The thermal free radical polymerization may be initiated by heating the polymerization mixture (e.g., by heating the LEAPS cell), for example, to about 40 to 45° C., for about 1 to 10 minutes, using an IR lamp, while maintaining the AC electric field at the electrolyte solution-electrode interface, to form a patterned film or polymer-microparticle composite.

The polymerization may also be triggered by irradiating the polymerization mixture with UV-light. For example, in the presence of the applied AC electric field, polymerization may be triggered by using a mercury lamp source. A wide range of wavelengths, spanning from about 250 to 340 nm, may be used, with exposure times ranging from about 15 seconds to about 10 minutes. In one preferred embodiment, the concentration of monomers in the polymerization mixture is about 10% by weight, and 2-hydroxy-4'-hydroxyethoxy-2-methylpropiophenone) may be used as the initiator to give a 1.5% by weight solution.

In certain embodiments, colloidal particles which are anionic or cationic particles ranging from about 0.5 µm to about 15 µm in diameter are used. In certain preferred embodiments, these particles are functionalized by attaching a variety of chemical functional groups to their surfaces. The process of forming composite gel-particle films may be readily extended to particles that display biomolecules attached on their surfaces, such as receptors or ligands. In certain embodiments, oligopeptides, proteins, oligonucleotides or nucleic acid fragments may also be attached to the particle surfaces. The particles may also be encoded by use of a chemically or physically distinguishable characteristic that uniquely identifies the biomolecules attached to those particles, an example of which includes color encoding the particles using fluorophore or chromophore dyes. Such a process allows chemical immobilization of functionalized microparticle assemblies or arrays for a variety of biochemical assays, including binding and functional assays. Examples 6 to 9 describe a number of these assays.

Figure 15:
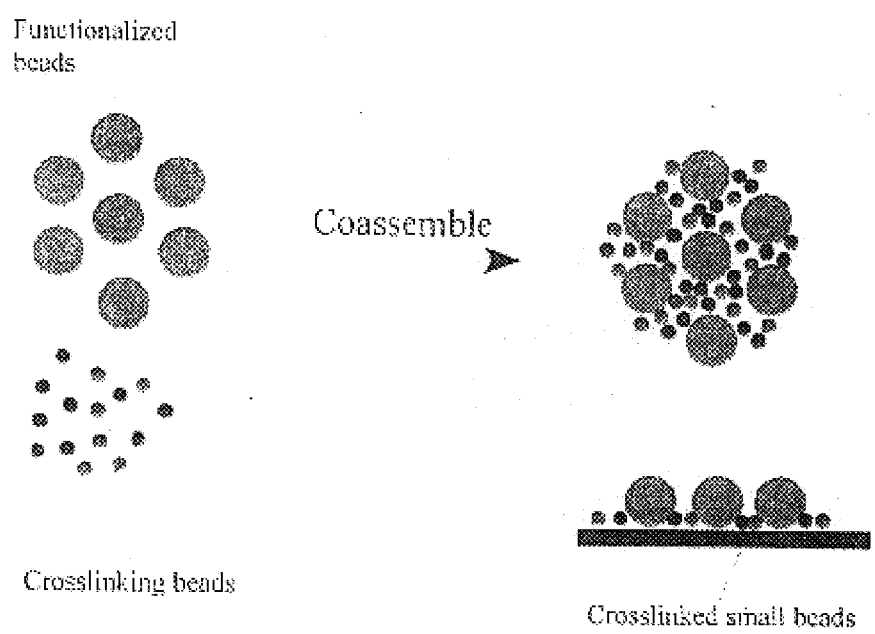
FIG. 15 is an illustration showing a heteroparticle arrays.

LEAPS also enables the co-assembly of a binary mixture of smaller beads along with larger assay beads in designated areas of the substrate (FIG. 15). Once arranged in an array format, the smaller beads undergo two-dimensional crosslinking due to electrostatic interactions or reactions between chemical moieties on the surfaces of neighboring beads. The two-dimensional crosslinked aggregate created in this process acts as an inert mold for the larger assay beads and thereby immobilizes them. The advantages of the protocol include the ease of implementation, control of spatial localization and good immobilization efficiency.

In certain embodiments, the particles used in preparing polymer-microparticle composites may be magnetic. In certain other embodiments, examples of the particles used are eukaryotic or prokaryotic cells, or liposomes. The polymer-microparticle composites produced using these particles may also be used in various biochemical assays, including the assays described in the Examples.

The particles useful in the preparation of the composite may also comprise inorganic particles, including metal particles, semiconductor particles and glass particles. The inorganic particles may also be coated with a polymeric shell.

Fabrication of a Gel-Embedded Planar Array of Vesicles

There is a growing interest in developing miniaturized sensing, sampling and signal amplifying structures coupled with an analytical measuring element to carry out a variety of bioassays. The sensing component typically reacts or interacts with an analyte of interest to produce a response that can be quantified by an electrical or optical transducer. The most common configuration uses immobilized biomolecules on solid phase supports while another less common approach uses living microorganisms or cells or tissues as the sensing structure.

Unilamellar vesicles are composed of a single lipid bilayer shell that encloses an entrapped aqueous compartment. Methods have been described to prepare giant unilamellar vesicles with sizes approaching that of cells. Such vesicles are attractive as ultra-small reaction vessels or "artificial organelles" in which the reaction is confined and separated from an external medium. Vesicles containing reconstituted integral membrane proteins provide a synthetic chemical structure to study the function of such proteins, including many cell surface receptors. In addition, the surface of such vesicles can be decorated with a variety of receptor moieties that mimic a natural cell, thereby allowing complex biochemical reactions and/or interactions to be studied (Lasic, D. D. Ed. "Liposomes: From Physics to Applications", $1^{st}$ ed., Elsevier Science B.V.: Amsterdam, 1993.)

Given a mixture of two types of vesicles, each containing one of the reactants of a reaction of type A+B→C, two vesicles of different type may be brought into close proximity, (e.g., by forming a close-packed planar array). By applying a pulsed electric field in accordance with methods known in the art, the vesicles are fused to form a larger vesicle in which the reaction A+B→C can now occur. In a preferred embodiment, "A" may represent an enzyme, "B" a substrate, and "C" the product of the enzyme-catalyzed reaction. This reaction scheme may be generalized to involve more than two reactants.

Vesicles entrapping a single functionalized and encoded microparticle can also be prepared by methods known to the art. Using methods of this invention, microparticle encoded, gel-embedded vesicle arrays may be prepared to provide a synthetic assay format in which the function of multiple cell-surface receptors such as ion channels may be quantitatively characterized.

Figure 17:
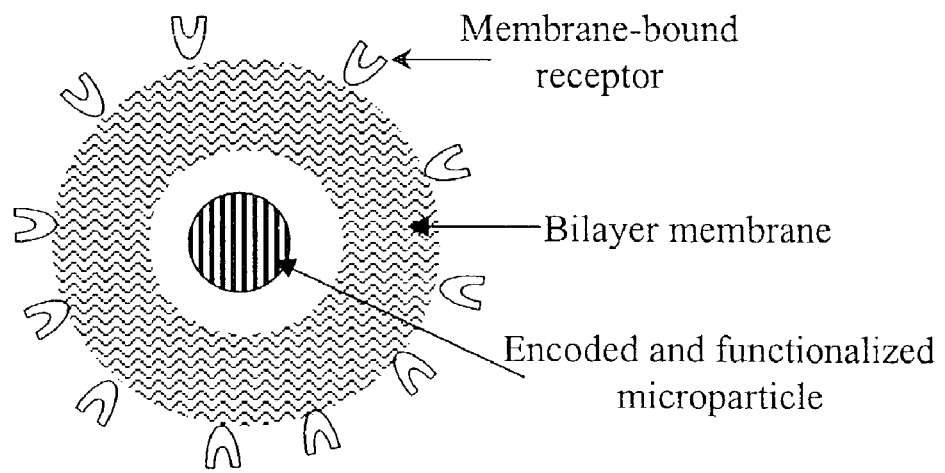
FIG. 17 is an illustration showing microparticle-encoded vesicles embedded in a gel film.
Figure 17:
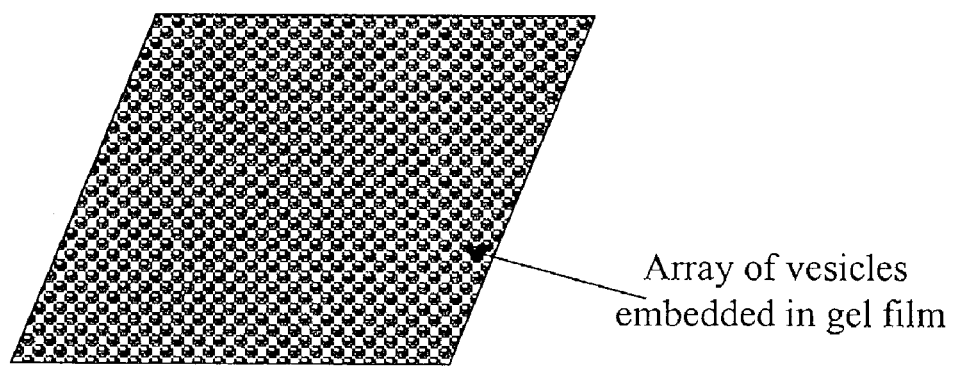

A variety of complex biochemical assays may be performed using such a composite structure. As illustrated in FIG. 17, an array of vesicles displaying multiple types of receptors is immobilized in a thin gel film using methods disclosed herein. In this embodiment, each vesicle displays only one type of receptor and contains a corresponding fluorescently stained and functionalized microparticle. In the course of performing the assay, the fluorescent color of the particle is used to determine the identity of the receptor on the vesicle. In addition, the microparticle is also functionalized on its surface with a measuring element, such as an environmentally sensitive fluorescent dye, in order to indicate a change in the internal aqueous compartment of the vesicle following a binding event on its surface.

Patterned Materials

The ability to grow complex materials with small feature sizes is of much interest for the fabrication of structured and multifunctional films, biologically relevant heterostructures and photonic materials for optical and optoelectronic applications. Thus, processes to form patterns rapidly and directly to give geometrically as well as functionally organized structures without using complicated etching process or complicated chemical schemes can be extremely useful. In accordance with the present invention, the LEAPS-directed formation of patterned gel and gel-particle composites provides for the fabrication of a variety of inorganic-organic, organic-organic, or fully inorganic composite structures.

Organic-organic composite—After formation of the patterned gel film on the low impedance areas of the substrate, the high impedance regions of the substrate can be decorated with a second polymer preferably through a process other than bulk radical polymerization (employed to synthesize the gel). For example, if the substrate is silicon, regions of high and low impedance can be obtained by forming a patterned silicon oxide film on the surface of the silicon substrate. In this case, the regions where the oxide layer is relatively thicker correspond to regions of higher impedance. The high impedance silicon oxide-capped regions can be modified by covalently bonding siloxane polymers or oligomers, adsorbing polyelectrolytes, and/or adsorbing functional groups that are hydrophobic or capable of hydrogen bonding. Following such a process, the earlier gel layer can be lifted off, producing a complementary patterned polymer or gel film.

Figure 8:
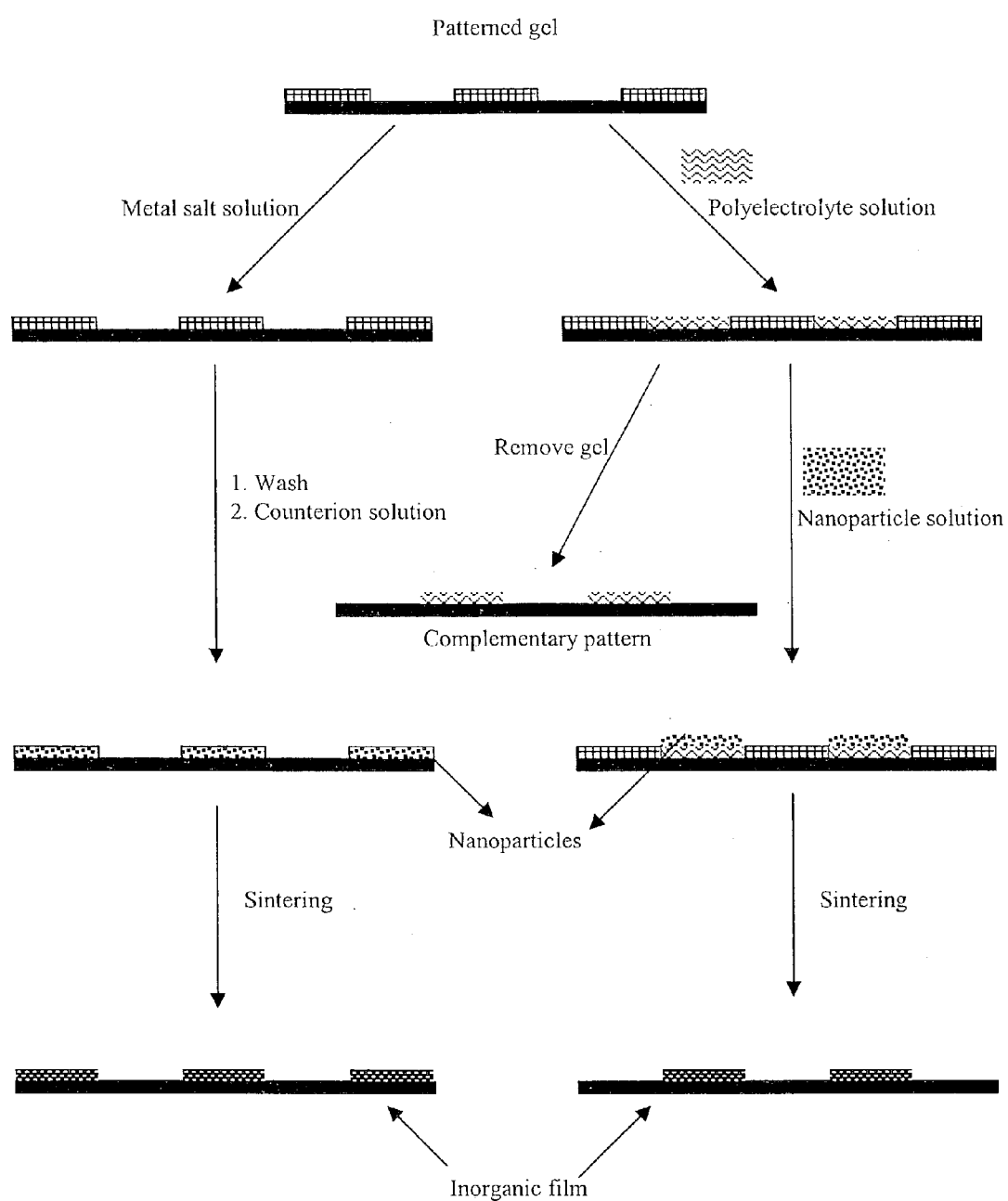
FIG. 8 is an illustration showing a process to produce inorganic-organic hybrid films.

Organic-inorganic composite—FIG. 8 outlines the basic procedure for making metal (Au, Ag, Cu, etc.), metal oxide ($Fe_2O_3$, $Co_3O_4$, NiO) or semiconductor (CdS, PbS, ZnS) nanoparticles in the patterned gel matrix. The process involves exposing the patterned gel on a substrate to a solution of a metal salt, followed by DI water rinse and exposure to reducing agent (in case of the metal) or second salt solution in other cases. The nucleation and growth of the nanoparticles take place within the hydrophilic domains defined by the gel film.

Inorganic composite—Fully inorganic structures can be generated from the structures above by calcining at high temperatures so as to burn off the organic component.

Interconnections

The realization of interconnections in the form of electrical, optical, or chemical conduits in small devices represents a critical aspect of the realization of integrated electronic, optoelectronic, or biochemical processors and apparatus. The method of the present invention permits the assembly of linear microparticle assemblies in accordance with LEAPS, either under illumination or on patterned electrolyte-insulator-semiconductor (EIS) interfaces, and their subsequent immobilization, for example by embedding within a gel matrix as described herein.

Electrical Conduit—Following the assembly of metal core/polymer shell particles into linear configurations, rapid heating of the silicon substrate, for example by exposure to pulsed laser light, will melt away the polymer components and fuse adjacent metal cores. Of interest in this application will be particles containing solid metal (Cu, Ni) cores or particles containing metal nanoclusters dispersed into a polymer matrix which may be prepared by methods known to the art.

Optical Conduit—Within a linear assembly of glass particles, illuminated with focused light, particles will guide scattered or emitted light to their respective nearest neighbors. Thus, individual beads that are illuminated by focused laser light can serve as secondary sources to illuminate adjacent particles within the linear assembly.

Chemical Conduit—Following the assembly of polymer particles into linear, circular or other desired configurations, particles may be permanently immobilized on the substrate, for example by non-specific adsorption. The resulting structure may serve as a positive mold around which a gel matrix can be grown. When the gel matrix is then lifted, a complementary negative surface relief is revealed. Such structures can be closed by fusion with a substrate or another gel and can serve as linear conduits for the transport of biomolecules or other materials.

Self-Supporting Flipped and Cleaved Gels and Polymer-Microparticle Films

The present invention provides novel patterned films and/or polymer-microparticle composites, including a planar assembly or array of particles embedded in a gel (i.e., a single layer, or substantially single layer assembly). In preferred embodiment, these gels are prepared according to the methods described above.

As discussed previously, the patterned polymeric films and the polymer-microparticle composites of various types may be produced, for example, by varying the monomer concentration.

In one embodiment of the present invention, a self-supporting film (preferably a hydrogel) is prepared. In one example, the concentration of monomers in the polymerization is greater than about 10% by weight. Preferably, acrylamide monomers are used. Following the polymerization, the LEAPS microcell may be dismantled with the gel matrix attached to the first electrode. The hydrogel produced is self-supporting and a free-standing patterned gel film may be obtained simply by peeling off the film from the second electrode. The film is stable in aqueous solution and stays intact for months. An example of such a free standing gel is shown in FIG. 2b. In addition to the substrate-supported and self-supporting gel films described above, a "Lift-Off" processes may be used to obtain polymeric films and/or composites that are detached from the light-sensitive (or patterned) bottom electrode. In one example, a vinyl siloxane coated second electrode is in the microcell. The vinyl siloxane coating allows covalent tethering of the gel film on the second electrode. Beads, suspended in a solution containing all ingredients required for subsequent in-situ gel formation, are assembled in designated regions of the light-sensitive (or patterned) electrode using an AC-electric field at a given voltage and frequency.

Figure 4A:
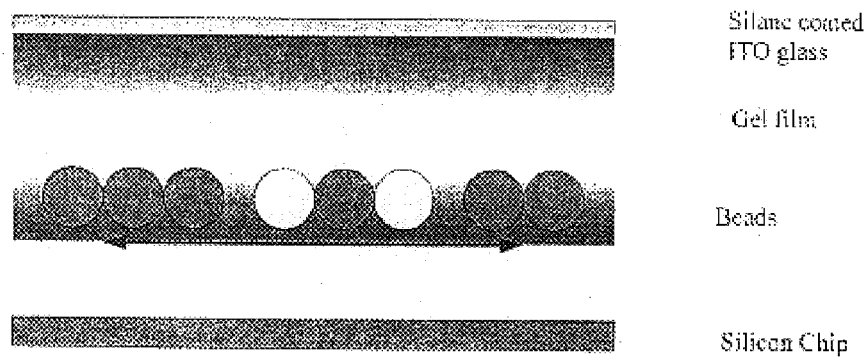
FIG. 4a is an illustration showing a flipped gel-particle composite.

Keeping the field switched on, the microcell may, for instance, be irradiated with UV-light from a 150 W Hg source for about 3 minutes. Afterwards, the UV illumination and field are switched off and the microcell is opened by separating the first electrode from the second electrode: the covalent attachment of the gel to the second electrode ensures that the gel remains adhered to the second electrode and readily separates from the first electrode. By inverting the substrate-attached gel film, beads displaying receptors capable of binding the molecules of interest are located at the outer, exposed surface of this inverted or "flipped" gel ("FlipGel"). Thus, the diffusion length of the molecules to migrate from the solution above the gel to the bead surface is small compared to that in the case of non-inverted regular gels (see FIG. 4a). An assay then may be conducted on the gel-embedded bead array by exposing the gel to the solution containing analyte molecules of interest.

Figure 4B:
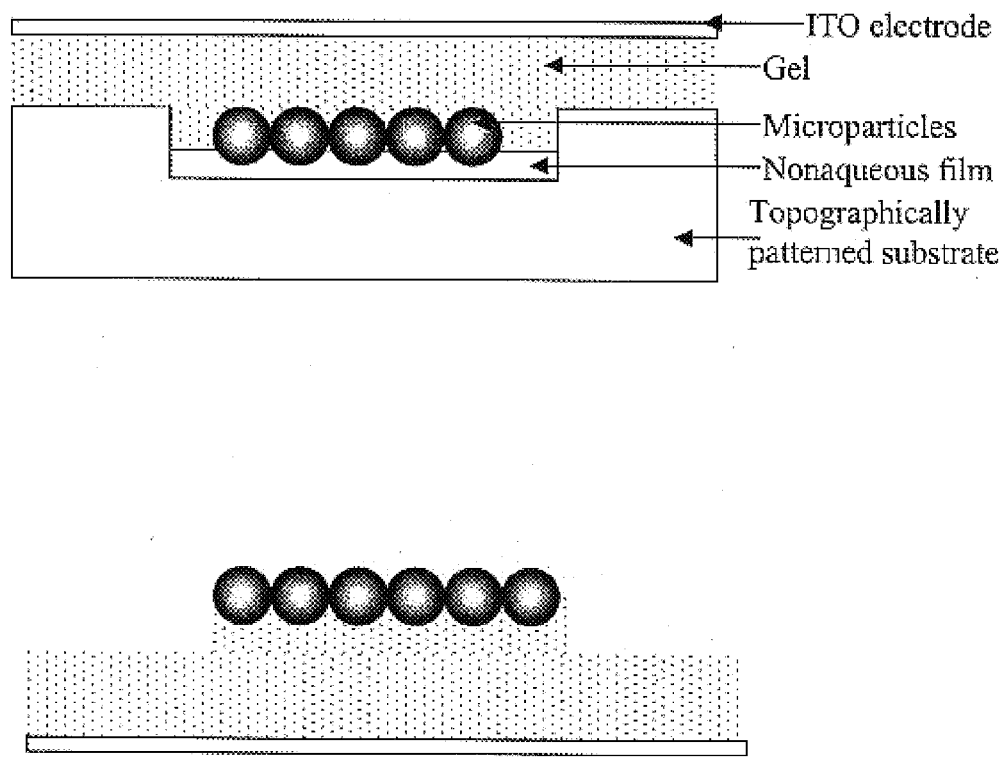
FIG. 4b is an illustration showing a flipped gel-particle composite with the particles partially exposed.
Figure 5:
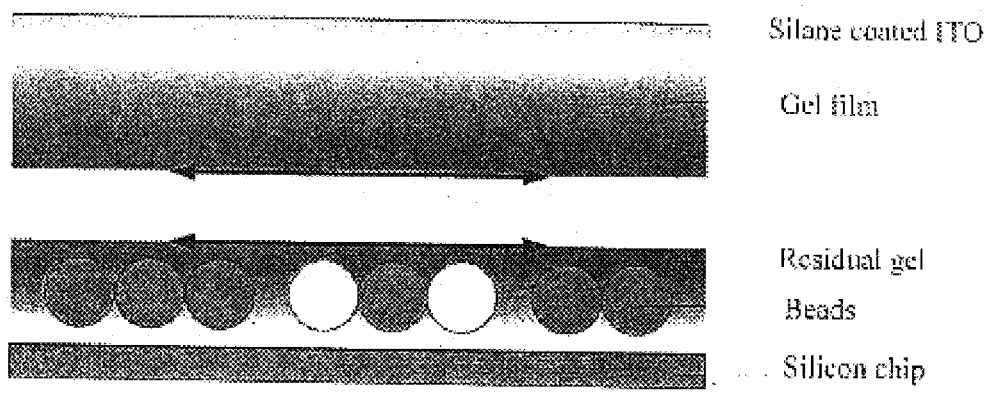
FIG. 5 is an illustration showing a cleaved gel-particle composite.

In certain other embodiments, the position of the bead array relative to the outer bounding surface of the embedding gel film may be controlled by assembling the microparticle array on a topographically patterned electrode surface. In these embodiments, designated recesses of defined depth containing a non-aqueous phase that is non-miscible with an overlaid aqueous phase containing the microparticles are exposed. The non-aqueous phase is also non-miscible with the chemical constituents required for gel film formation in accordance with the previous protocols (see FIG. 4b). Upon application of the requisite AC electric field, microparticles assemble within the designated recesses in such a way as to permit particles to remain partially submerged within the organic phase deposited into the recesses prior to assembly. Following assembly, gel formation is initiated in the manner described; however, the immiscibility of the two layered phases ensures that polymerization is confined to the aqueous phase, thereby leaving embedded microparticles partially exposed In certain other embodiments, a cleaved gel is prepared, following the same principle as FlipGels. The basic differences are that (a) the monomer concentrations used in the polymerization reaction are smaller (for example, ≦5% by weight) and (b) the time of irradiation is shorter. Under these conditions, the degree of polymerization is not uniform throughout the thickness of the cell. Typically, the degree of polymerization and crosslinking is highest near the second electrode and progressively grows weaker as one approaches the first electrode. After gelling, disassembling the microcell, and pulling the two electrodes apart, the gel typically fractures at a plane very close to the substrate surface (see FIG. 5). Thus, a layer of gel remains attached to the second electrode while the first electrode retains the rest of the gel containing the assembled bead arrays. The first electrode, with the assembled bead array, can now be used for a variety of assays with the assay solution location directly on top of the bead-containing gel. In this application, the diffusion length of the molecules is reduced from that of a regular gel because the cleavage usually occurs just over the plane containing the bead array, leaving the beads more accessible to molecules present in the solution above the gel.

DNA Electrophoresis and Hybridization in Gel-Microparticle Hybrid Films

Figure 11:
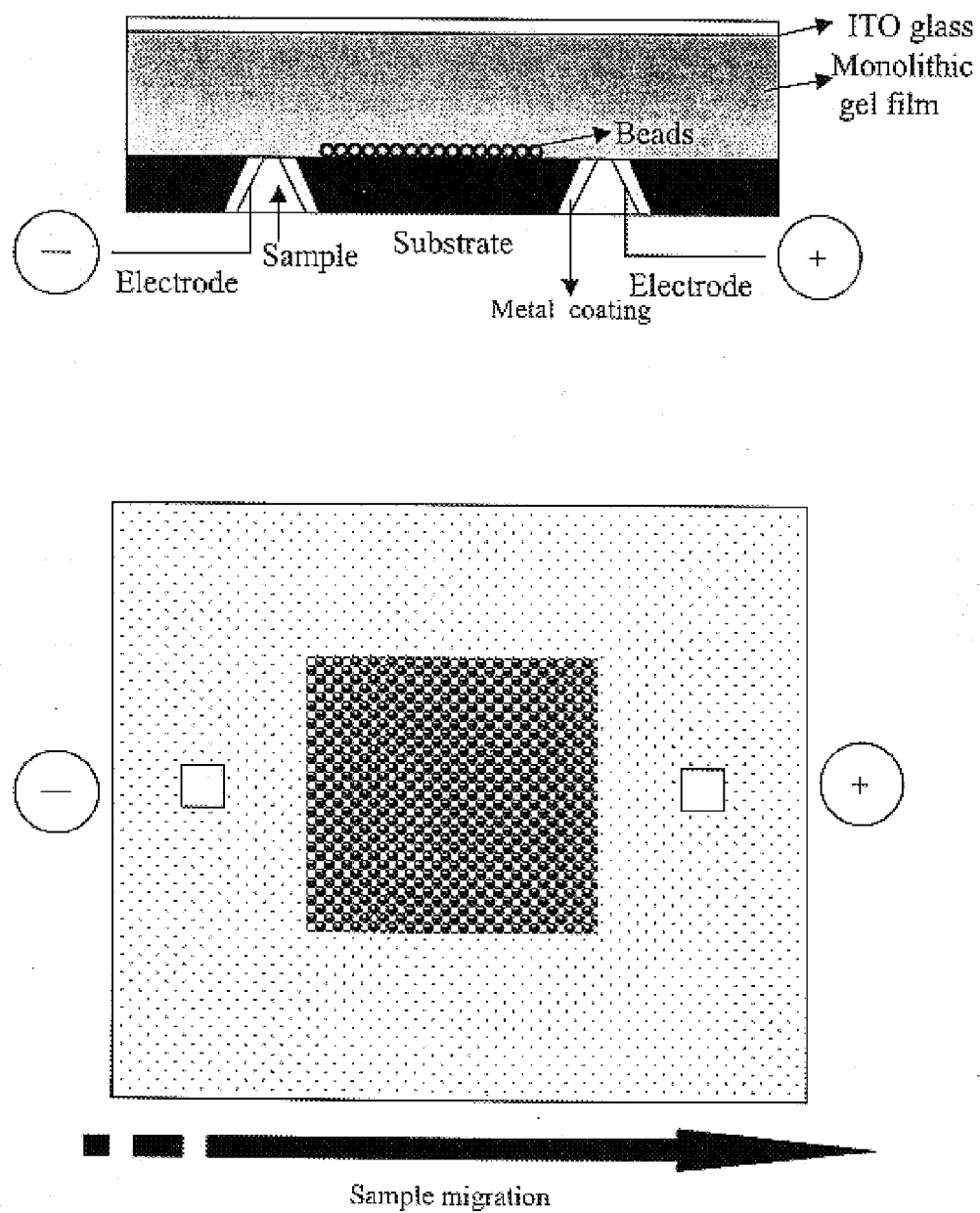
FIG. 11 is an illustration showing electrophoretically assisted DNA hybridization.

One method of performing rapid nucleic acid hybridization assays in gel-microparticle hybrid films involves the use of DC electric fields to induce electrophoresis of target nucleic acid strands. This method is especially suitable in applications where large target fragments are present for which diffusion inside the gels is expected to be slow. Typically the samples for analysis are denatured and electrophoresed through gel-microparticle hybrid films. As the complementary single-stranded nucleic acid targets contact the capture probe (oligo) functionalized beads, they hybridize and are quantitatively immobilized on the microparticle surface. The non-complementary strands do not hybridize with the capture probe and continue to migrate through the gel. The hybridization is detected using luminescent labels associated with the sample nucleic acid. FIG. 11 shows two different possible geometries for carrying out electrophoretically assisted hybridization in gel-microparticle hybrid films.

Reversible Immobilization of Microparticles within Gel Films

The process of forming polymeric films and polymer-composites involves synthesis of chemically crosslinked polymers. The process of forming composite gel-particle films according to this invention can, however, easily be extended to include physically gelling systems such as block copolymer gels, agarose gels, gelatin gels etc. Such gels consist of polymeric networks held together by physical rather than chemical crosslinking. The reversible gelation of such systems may, for example, be triggered thermally with the system existing as a sol at a high temperature and transforming into a gel on cooling and vice versa. The reversibility and the capability to form and to immobilize bead arrays at will allows one to carry out dynamic on-chip bioassays.

Figure 7:
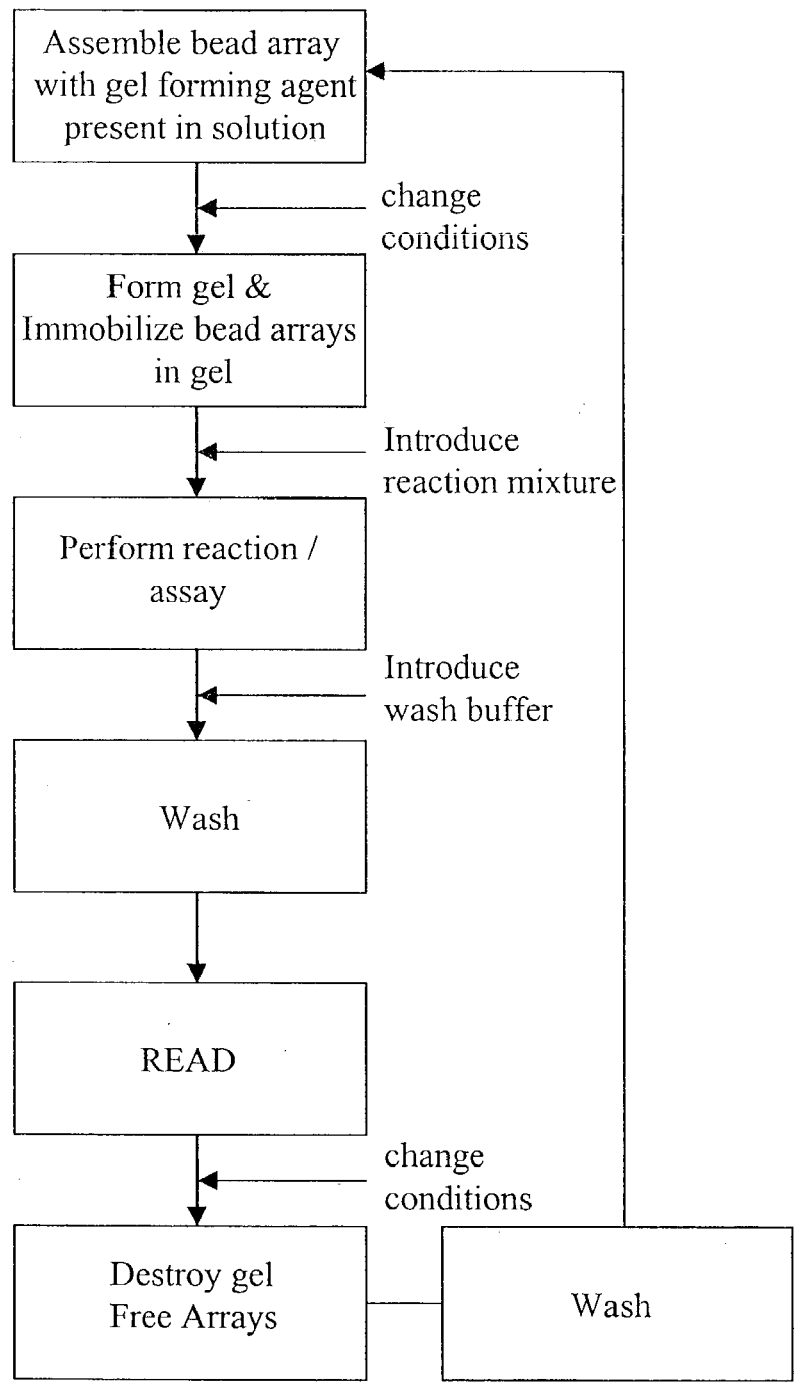
FIG. 7 is an illustration showing a process to produce a gel-particle composite by reversible gelation.

The flowchart in FIG. 7 summarizes one possible protocol for performing an assay using a reversible gel. The protocol begins with the formation of a bead array in the presence of a solution that contains a gel-forming agent. After the bead array is formed (for example using LEAPS as disclosed in U.S. Pat. No. 6,251,691), a gel is formed to immobilize the beads. Further processing steps, such as peeling to produce a Cleaved Gel or a FlipGel may be optionally performed prior to introducing the reaction mixture for the assay. After the assay, the gel is washed and the reaction products are detected, for example by monitoring a fluorescent signal that indicates the presence or absence of a particular reaction. A method of detection known as READ may be used, as described below. After detection, the gel is destroyed to liberate the beads in the gel. Following a subsequent washing step, the beads may be used again in other reversible gel assays. One method of performing the detection step in FIG. 7 is to use a protocol known as READ (Random Encoded Array Detection), as described in detail in PCT/US01/20179 hereby incorporated by reference). In this method, an image of the bead array is taken before the assay (i.e, a decoding image) and compared with an image of the bead array taken after the assay (i.e., an assay image). The decoding image is taken to determine the chemically and/or physically distinguishable characteristic that uniquely identifies the binding agent displayed on the bead surface, e.g., determining the identity of the binding agents on each particle in the array by the distinguishable characteristic. The assay image of the array is taken to detect the optical signature of the binding agent and the analyte complex. In certain embodiments, fluorescent tags (fluorophore dyes) may be attached to the analytes such that when the analytes are bound to the beads, the fluorescent intensities change, thus providing changes in the optical signatures of the beads. In certain embodiments, the decoding image is taken after the beads are assembled in an array and immobilized and before taking the assay image, preferably before contacting the binding agents on the beads with an analyte.

The identity of the binding agent of the binding agent-analyte complex is carried out by comparing the decoding image with the assay image.

In preferred embodiments, images analysis algorithms that are useful in analyzing the data obtained from the decoding and the assay images may be used to obtain quantitative data for each bead within an array. The analysis software automatically locates bead centers using a brightfield image of the array as a template, groups beads according to type, assigns quantitative intensities to individual beads, rejects "blemishes" such as those produced by "matrix" materials of irregular shape in serum samples, analyzes background intensity statistics and evaluates the background-corrected mean intensities for all bead types along with the corresponding variances.

EXAMPLES

The present invention will be better understood from the Experimental Details and Examples which follow. However, one skilled in the art will readily appreciate that the specific methods and results discussed are merely illustrative of the invention described in the claims which follow thereafter.

Example 1

AC Electric Field-Mediated Formation of Patterned Gel Films

LEAPS is carried out in a fluidic microcell formed by sandwiching a double-sided Kapton spacer of ~100 μm thickness (between a 1 cm×1 cm silicon chip, n-type, capped either by a uniform or a lithographically patterned thin $SiO_2$ layer), also serving as the bottom electrode, and a glass cover slip coated with indium tin oxide (ITO) to a typical sheet resistance of 1400 Ohm Square serving as the top electrode. FIG. 1 illustrates the various components of a LEAPS microcell.

The mixture of monomers and the initiator is introduced within the LEAPS cell and the electric field is applied. The thermal free radical polymerization is then initiated by heating the cell ~40–45° C. using an IR lamp (the polymerization can also be triggered by a step change in the bias voltage from a large positive value to a small positive value). Typical parameters of the AC electric field used for this particular example are Vp-p~5–8V and ω~1 kHz. This AC electric field-mediated protocol leads to the formation of a thin layer of hydrogel in predesignated areas (low impedance regions) on a $Si/SiO_2$ substrate.

Hydrogels are formed using azodiisobutyramidine dihydrochloride as a thermal initiator at a low concentration ensuring that the overall ionic strength of the polymerization mixture falls in the range of ~0.01 mM to 0.1 mM. The hydrogels are composed of a mixture of acrylamide and bisacrylamide of varying monomer concentrations from 20% to 5% (acrylamide: bisacrylamide=37.5: 1, molar ratio).

Figure 2:
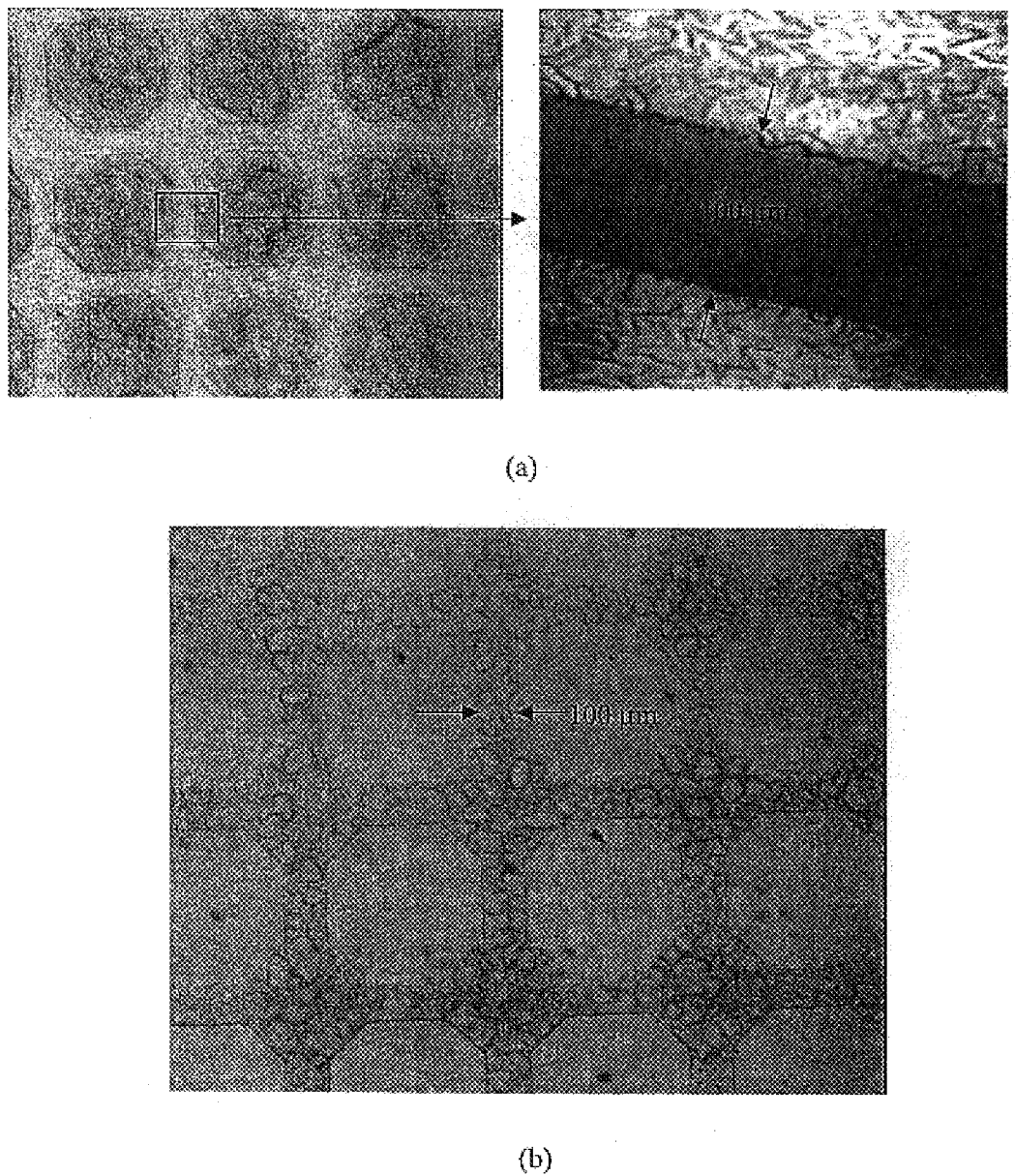
FIG. 2a contains a photograph showing a patterned gel film and a second photograph showing a close-up of a section of the film.
FIG. 2b is a photograph showing a free-standing gel film imaged in aqueous phase.

FIG. 2 illustrates a hydrogel formed on an interfacially patterned silicon substrate under the influence of an AC electric field. The gel is formed exclusively in the low impedance regions (thin oxide) of the substrate. The wrinkled pattern seen on the hydrogel surface is caused by a mechanical instability set up in the gel during polymerization (Tanaka, T., 1987, Nature, 325:796; Warren, J. A., 1995, Spatio-Temporal Patterns, Ed. Cladis, P. E. and Palffy-Muhoroy, Addison-Wesley. 91–105).

Example 2

Preparation of Gel-Microparticle Hybrid Films

A two stage process is used to synthesize polymer-microparticle composites. First, ordered particle arrays are formed from a microparticle suspension that also contains all of the ingredients required for subsequent in-situ gel formation in accordance with Example 1. LEAPS (see Example 1) is used to form arrays from particles suspended in a low viscosity dispersion of monomer(s) mixed with an initiator in accordance with Example 1. Second, gels are formed, either via heat-initiated in-situ polymerization (Example 1) to form spatially patterned hybrid gels (see FIG. 3(a)) or via UV-initiated in-situ polymerization to form monolithic hybrid gels (see FIG. 3(b)), as described below.

To assemble particle arrays, an AC voltage chosen in the range of 1–20 $V_{p-p}$, with a frequency in the range of 100 Hz to several kilohertz is applied between the electrodes across the fluid gap. Fluid and particle transport and assembly are then monitored by video microscopy, which permits frame capture and digitization of frames for further analysis.

Prior to assembly, particles stored in buffer are centrifuged and washed with deionized and ultrafiltered (conductivity<50 S $cm^{-1}$) distilled water three times. At the last wash, the monomer/crosslinker and initiator solution is added in an amount so as to maintain the original concentration of particles. The initiator and/or the salt concentration is maintained at $\leq 1$ mM. The resulting particle suspension is applied to the LEAPS cell so as to fill the gap between the two electrodes Anionic and cationic particles ranging from 0.5 μm to 15 μm in diameter, composed of silica, modified polystyrene or other polymers and functionalized with a variety of chemical surface groups, as well as functionalized core-shell particles obtained from a variety of manufacturers are used.

Figure 3:
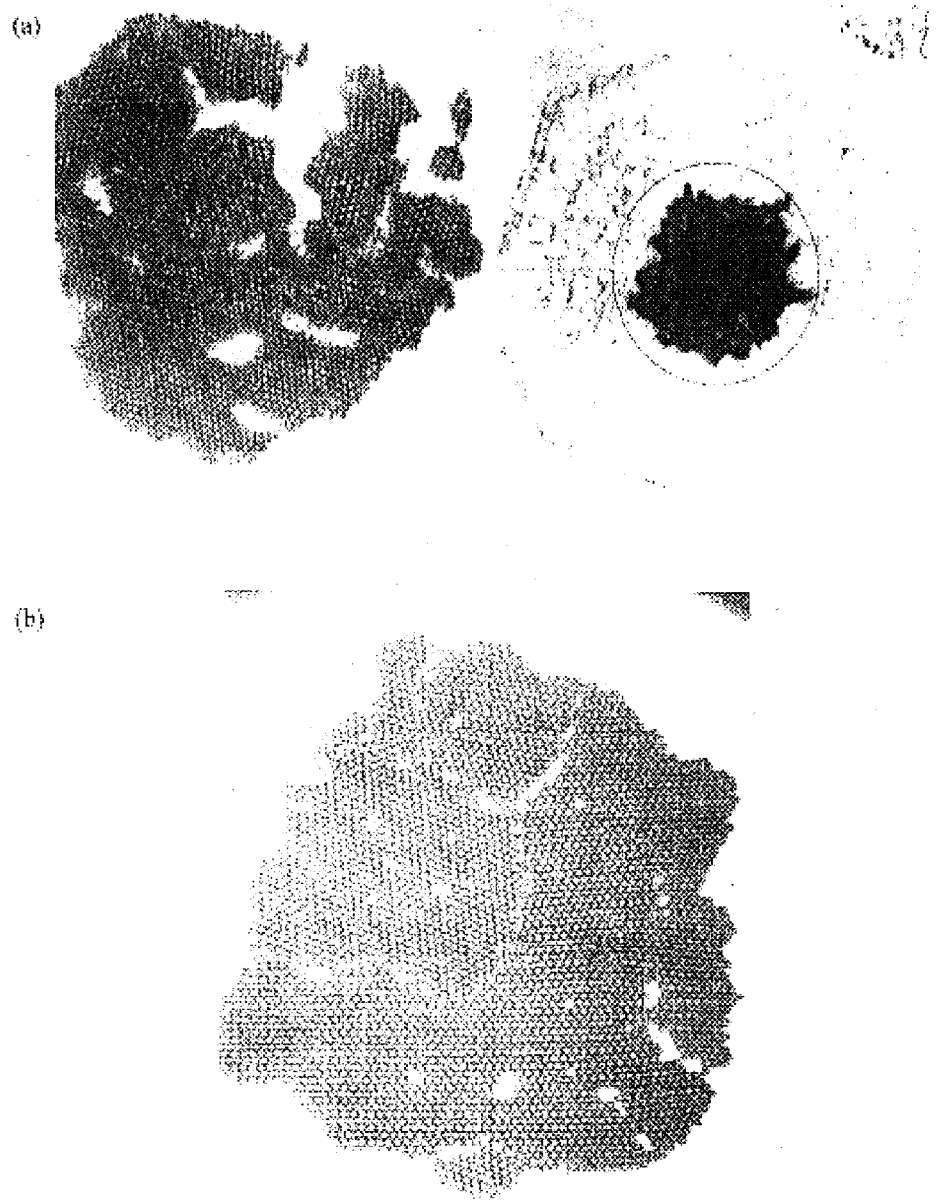
FIG. 3a contains a photograph showing a patterned gel-microparticle composite created via thermal initiation and a close-up of the central section of the composite.
FIG. 3b is a photograph showing a monolithic gel-microparticle composite created via UV-initiation.

Following array assembly, polymerization of the fluid phase is triggered in the presence of the applied AC voltage, by for example, using a mercury lamp source to effectively entrap the particle array within the gel. A wide range of wavelengths, spanning from about 250 nm to about 340 nm, is suitable for the polymerization. FIG. 3 shows an example of a particle array immobilized in a polyacrylamide matrix. The concentration of the monomers was 10% and the initiator used was a UV initiator Irgacure 2959® (2-hydroxy-4'-hydroxyethoxy-2-methylpropiophenone, Ciba Geigy, Tarrytown, N.Y.). The initiator was added to the monomer to give a 1.5% by weight solution.

Example 3

Self-Supporting Magnetic Gel Films

In one embodiment, free standing gel microparticle hybrid films similar to those described in the detailed description section are prepared according to the invention using functionalized and superparamagnetic microparticles or a mixture of superparamagnetic particles with (non-magnetic) color-encoded and functionalized microparticles. Incorporation of magnetically responsive particles permits the separation of the gel film from a solution containing a biological sample or samples by application of a magnetic field.

This is of particular benefit in carrying out multi-step biological assay protocols.

Figure 9:
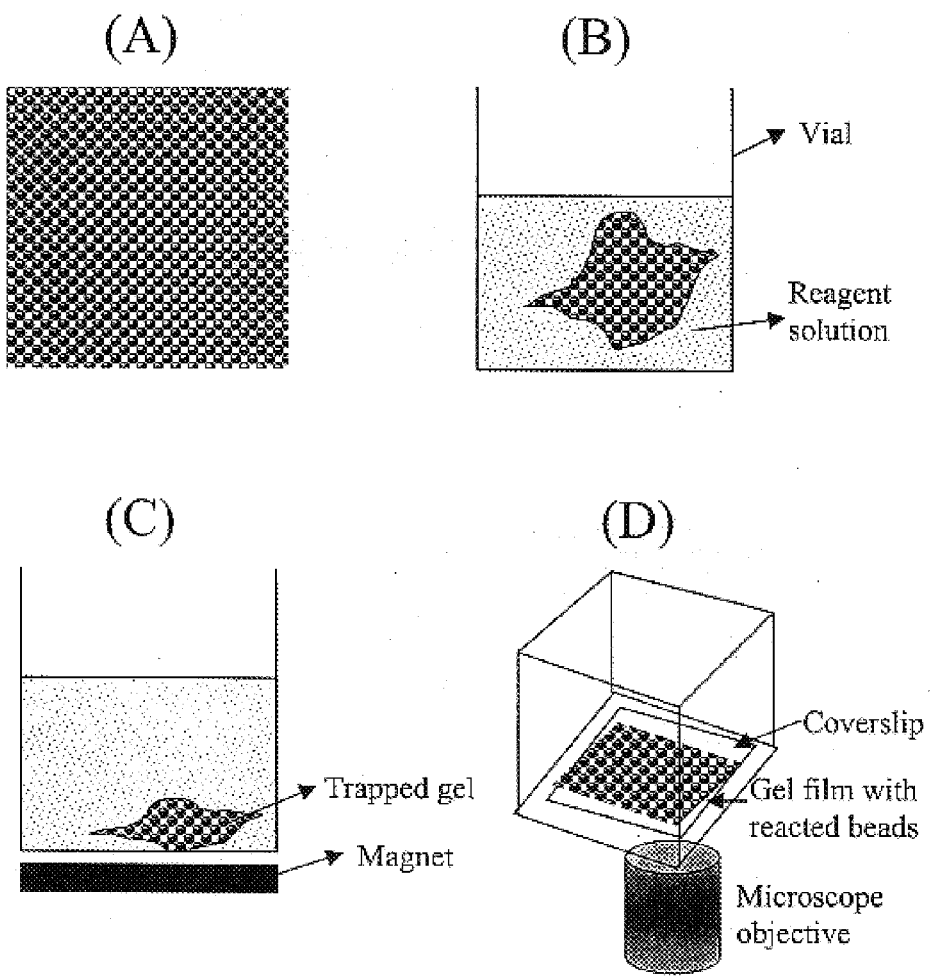
FIG. 9 is an illustration showing a process to produce and to characterize a magnetic gel-particle composite.

In a protocol involving the self supporting magnetic gel films of this invention (FIG. 9a), an in-tube binding assay that probes analyte molecules in solution through their capture by receptors on beads is performed under conditions permitting the magnetic gel-microparticle film to remain in suspension (FIG. 9b). Following completion of the assay, magnetic separation (FIG. 9c), achieved by application of a magnetic field, permits the temporary immobilization of the gel film on a transparent surface of the reaction chamber. Following fluid and/or buffer exchange, all excess fluid is removed in the last step, leaving the hydrated gel film exfoliated on the transparent surface even in the absence of the magnetic field (FIG. 9d). Images recording the results of the binding assay may now be obtained using a microscope. In a preferred embodiment, a coverslip is positioned above the film to prevent evaporation, which may lead to buckling of the film.

Example 4

Hybridization Assay in Gel-Microparticle Hybrid Films

DNA hybridization assays were conducted using oligonucleotide-functionalized particles embedded in gels. The oligonucleotide probe-coated particles were made as follows. Neutravidin-coated beads were washed thoroughly in salinated PBS of pH 7.4. The biotinylated probes were then added to the bead suspension and the mixture was incubated at room temperature for 90 min. The probe-coated beads are then stored in PBS solution containing 0.01% Triton.

The targets for DNA hybridization reactions can be either single-stranded or double-stranded molecules. Single-stranded DNA of a given length and sequence were synthesized chemically (Integrated DNA Technologies, Coralville, Iowa). A double stranded DNA target was produced from PCR-amplified products directly obtained from genomic DNA of patient samples. The PCR product was produced using fluorescence-labeled primers. After preparation, the primers were removed by a PCR purification kit (Qiagen) and the resultant solution was used in an assay. Single stranded DNA was prepared from a double stranded sample by digesting the antisense strand. For this purpose the antisense primers used in PCR amplification had a phosphate group at the 5' end. A strandase enzyme was then used to digest the antisense primer. In either case, the DNA at the end of the process was suspended in Tris-EDTA buffer and the concentration was determined using UV optical density measurements.

Before hybridization, the double stranded DNA was denatured to yield single strands. To achieve this, the DNA was diluted with Tris EDTA buffer and heated in a sand bath at 95° C. for 1 min. It was stored in ice before use. It was then mixed with an equal volume of tetramethylammonium chloride to yield the desired concentration of DNA for the reaction.

Two types of beads, internally stained with different fluorescent dyes and each bearing a different probe, were used for the reaction. One of the probes used was a prefect match with the target strand while the other sequence was mismatched.

The beads were washed three times with distilled water and suspended in 5% monomer solution and initiator concentration as described earlier. The beads were assembled into arrays in a LEAPS cell using 4 V peak-to-peak AC voltage and frequency 500 Hz. After assembly, the cell was irradiated with UV light for about 3 min. This yielded a Flip Gel which was then used in a hybridization assay. The Flip Gel was attached (gel-side up) to a polished silicon wafer using single-sided tape. One microliter of target containing 100 ng/μl DNA was diluted using 24 μl of TE and 25 μl of 2× TMAC. From the resultant solution 10 μl was added to the gel for reaction. The wafer was enclosed in an air-tight wafer holding container, sealed and set on a shaker at 50 rpm in an oven at 55° C. The reaction proceeded for 30 min. At the end of the procedure, the gel was washed twice in 1× TMAC equilibrated at 55° C.

Figure 10:
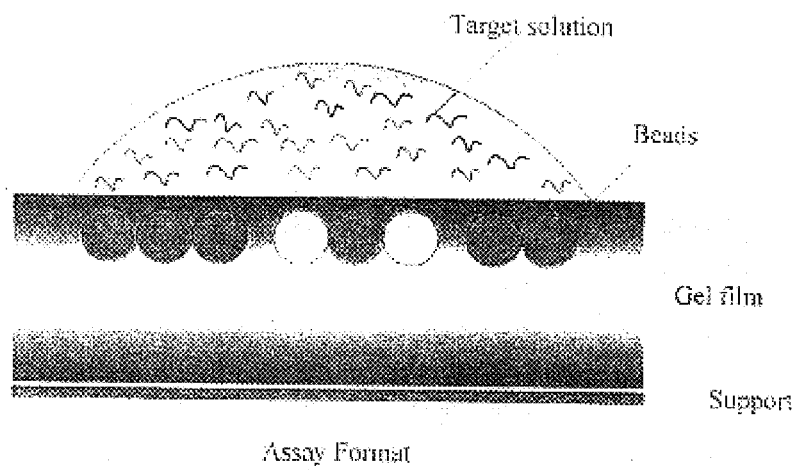
FIG. 10 is an illustration showing a DNA hybridization assay using a flipped polymer-gel composite. The set of four images obtained from analyzing the gel in different color channels were then analyzed to determined the results of the assay, as depicted in the bar graphs in FIG. 10.
Figure 10:
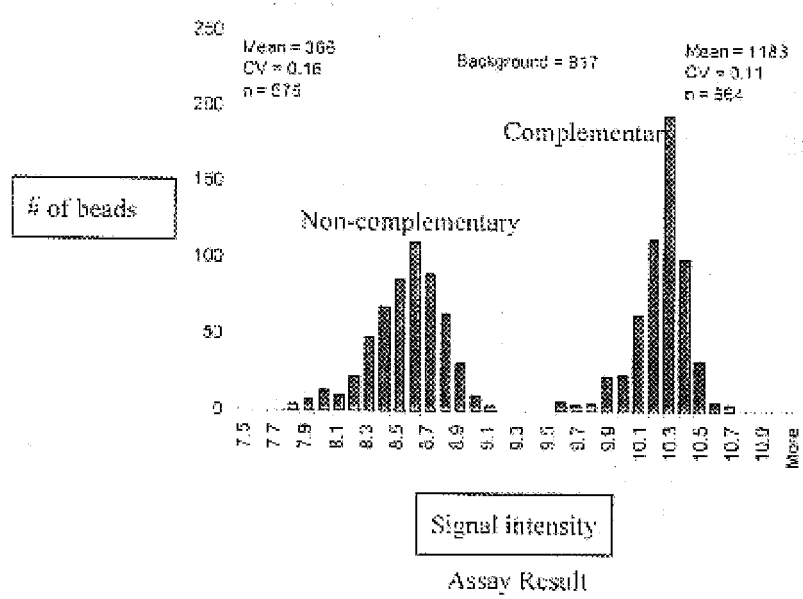

The gels were prepared for imaging by applying a coverslip on them. Bright field and Cy5 filtered images were recorded. To distinguish the two different types of particles in the arrays, images were also taken at two other color channels appropriate for the internal encoding dyes. The set of four images were then analyzed to determine the results of the assay (see FIG. 10).

Example 5

Immunoassay in Gel-Microparticle Hybrid Films

Protein assays are readily performed on supported gels, self-supporting gels, FlipGels and Cleaved Gels. An example of an immunoassay is the binding reaction between Mouse IgG and Goat Anti-Mouse IgG. For this reaction, the beads were surface-coated with the Mouse IgG. For this purpose, tosylated particles with a diameter of 3.2 μm were incubated overnight with the Mouse antibody (SigmaChem) in a phosphate buffer solution of pH 7.2. After the coating process, the particles are washed thoroughly with PBS containing bovine serum albumin.

The target molecules of goat anti-mouse IgG were labeled with a monofunctional fluorescent dye Cy5.5 (Amersham). The NHS-ester-containing dye was attached to the amine groups of the IgG according to a protocol supplied by the manufacturer. The dye and the IgG molecules were incubated for 1 hr at pH 9.3. The free dye was then separated from the labeled molecules using a gel filtration column and phosphate-buffered saline as the separation buffer. The concentration of IgG in the sample and the number of dye molecules per molecule of IgG was calculated.

Two types of particles are used for the reaction, one for the assay and the other as a negative control. They are distinguished by the use of internal encoding dyes which have excitation and emission wavelengths that are different from those of Cy5.5. One of the types of particles was coated with Mouse IgG as described above and the other only had a coating of neutravidin. A mixture of these two types of particles was collected by centrifugation and washed three times with de-ionized water containing 0.01% Triton. After the last centrifugation, the particles were suspended in a monomer mixture containing 10% monomer solution and UV-initiator in amounts described earlier. The particles were assembled in a LEAPS cell and irradiated to form a monolithic gel. Depending of the concentration and the time of irradiation, a regular gel, FlipGel or Cleaved Gel is formed.

Figure 12:
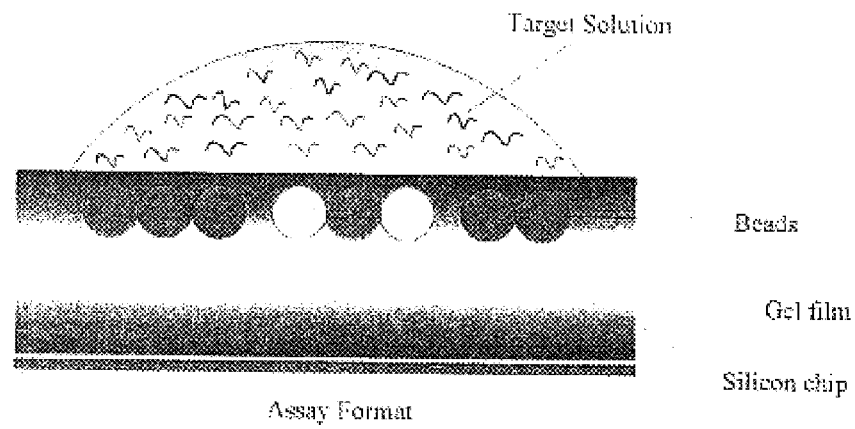
FIG. 12 is an illustration showing an immunoassay using a flipped polymer-gel composite. The set of four images obtained from analyzing the gel in different color channels were then analyzed to determine the results of the assay, as depicted in the bar graphs in FIG. 12.
Figure 12:
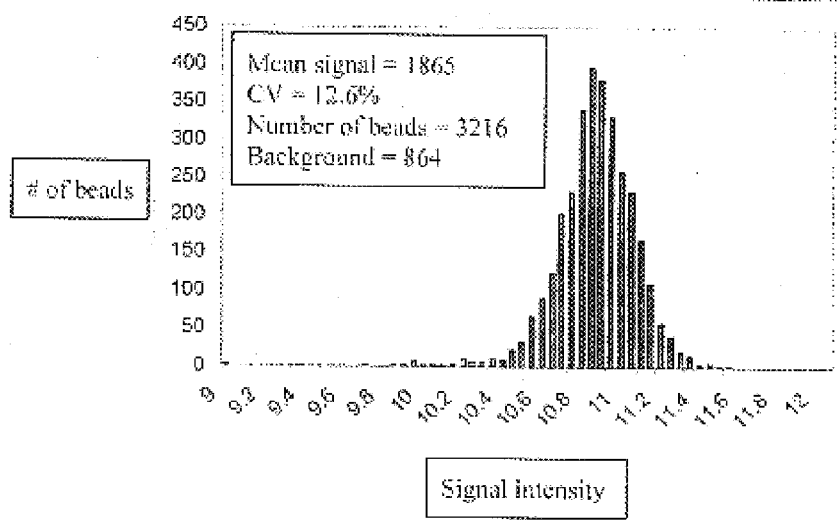

The gel is placed with the support (coverslide in case of FlipGel, silicon chip in case of regular and Cleaved Gels) gel side up. A given volume (10 µl) of a known concentration of the Goat anti-Mouse IgG placed on the gel. The gel with the solution is then enclosed in an airtight container and put on a shaker operating at 50 rpm in an oven at 37° C. for one hour. After binding has occurred, the gel was loaded with 20 µl of alkaline SDS (Tris base containing 10% SDS) for 30 min to reduce nonspecific binding. The gel was then washed with alkaline SDS twice and prepared for imaging. A coverslip was placed on the wet gel and images were taken in the bright field and in the Cy5.5 channel. To distinguish the two different types of particles in the arrays, images were also taken at two other color channels appropriate for the internal encoding dyes. The images were then analyzed to establish the mean binding intensity and the light intensity distribution of each type of bead in the mixture (see FIG. 12).

Example 6

Bioanalytical Assay with Integrated Filtering and Specific Capture

The gel-microparticle hybrid film is useful for selectively capturing specific nucleic acids or proteins from a crude mixture like whole blood or cell lysate. Typically, a crude sample containing whole blood is placed in contact with the gel containing microparticles that are functionalized with capture probe molecules of interest. The red and white cells are automatically screened by the gel on the basis of their size. The complementary components from plasma bind to the capture probe coated beads. Non-complementary components can then be easily washed off.

Example 7

Recording of Assay Images from Hybrid Films

In this invention, a Nikon Eclipse E-600FN epifluorescence microscope equipped with 150 W xenon-arc lamp was used for measurements. A Nikon 20×0.75 NA air objective, fitted with an optimized set of filter cubes for the selection of fluorophores also was used for all measurements. Images were recorded with a cooled 16 bit CCD camera (Apogee Instruments Inc.). The exposure/integration times for the various preparations varied between 25 to 500 ms. User interfaced programs for collection and analysis of images and assay results were developed using MATLAB™ which was run on a PC.

Example 8

Multiple Samples Per Chip

Figure 13:
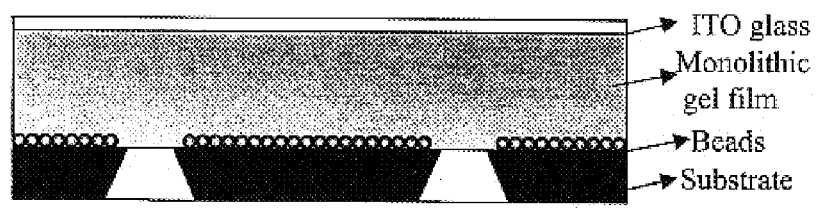
FIG. 13 is an illustration showing the analysis of multiple samples on a monolithic gel chip.
Figure 13:
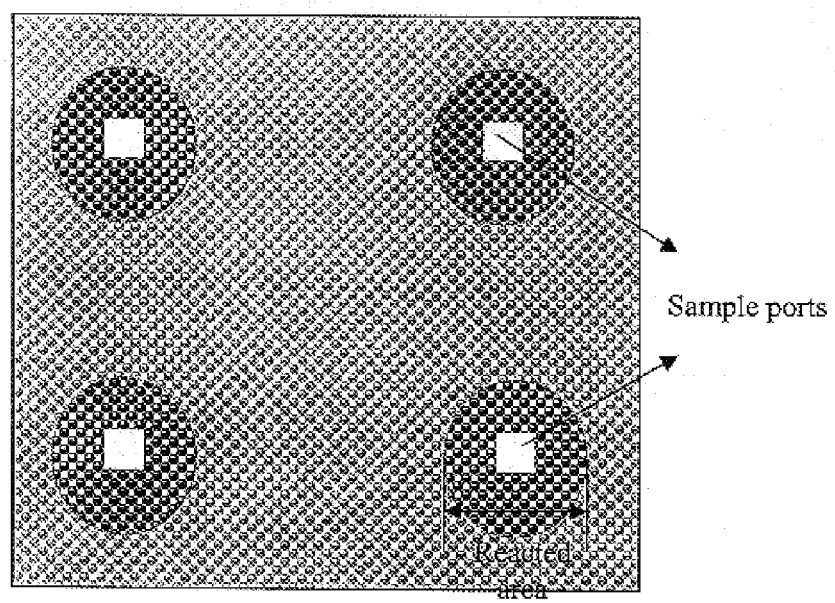

FIG. 13 illustrates a method of carrying out multiplexed assays for multiple samples using the same monolithic gel film containing multiple bead arrays. A gel film containing bead arrays is synthesized (as described in Example 3) on an interfacially patterned silicon chip into which through holes have been made at four corners (choice of this geometry is arbitrary and is chosen here for illustrative purposes only. In principle, a wide variety of designs and number of holes can be chosen. The samples are added by pipette to the holes in the back of the chip. The sample is allowed to spread diffusively and to react with the surrounding particles as shown in FIG. 13. Depending on the length of the incubation time the area of the reacted patch will vary (Area~tD, where t is the reaction time and D is the diffusion coefficient of the target in gel).

Example 9

Cell-Based Heteroreactor

Figure 14:
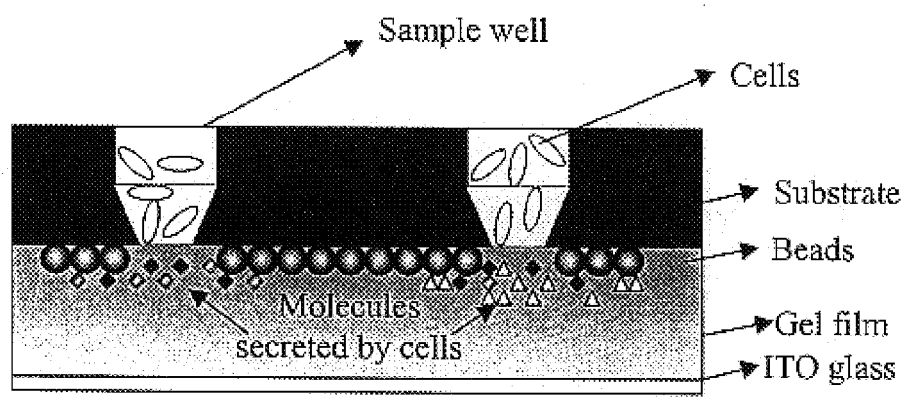
FIG. 14 is an illustration showing a process to implement a cell-bead heteroreactor.

A cell-based heteroreactor of this invention is constructed on a silicon substrate containing etched through-holes serving as fluidic interconnects. First, a gel-microparticle composite is formed in accordance with Example 3 in the fluidic compartment defined by the front side of the silicon electrode and the ITO-coated glass electrode. Next, suspensions of cells are introduced into the tapered etched through-holes on the backside of the silicon electrode. Molecules secreted from cells within these microwell structures are allowed to diffuse into the gel, as shown schematically in FIG. 14, where they are detected after being captured by functionalized beads within the previously assembled array. Alternatively, cells within the microwells may be lysed, and released genomic DNA may be enzymatically fragmented to allow sufficiently small fragments to diffuse into the gel where they are captured by hybridization to functionalized beads within the previously formed array. In this embodiment, constituents of the lysate that are larger than the pore openings of the gel are kept out. This second structure can remain open, and may be fashioned to exhibit the dimensions and form factors of various useful structures, such as a 1536-well microplate, for example. In other embodiments, a third delimiting planar substrate may be placed in contact with the back side of the silicon electrode, in order to form a second fluidic compartment that permits microfluidic transport of cell suspensions.

Example 10

Fabrication of an Enzyme Sensor by Directed Self-Assembly

In accordance with the methods of the present invention, the combination of LEAPS-mediated active assembly of an array of functionalized microparticles and the chemical synthesis of a polymeric gel film permits the in-situ synthesis of a variety of sensors.

Starting with a fluidic microreactor composed of a patterned silicon/silicon oxide chip and an ITO-coated glass electrode arranged in a sandwich geometry (FIG. 1), a glucose sensor based on a gel-microparticle composite is constructed by the following sequence of steps.

1—inject solution containing
functionalized particles displaying pH-sensitive or oxygen-sensitive dyes known to the art reaction mixture containing precursors and ingredients for gel formation
functionalized glucose oxidase 2—apply AC electric field according to LEAPS to produce microparticle arrays)

3—form gel by UV-initiated polymerization to form patterned or monolithic gel film incorporating functionalized glucose oxidase 4—remove electric field and UV illumination 5—inject glucose-containing sample into space below patterned silicon chip to initiate diffusion of sample into gel matrix; in the presence of glucose, the following reaction occurs

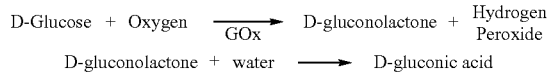

6—monitor reaction shown above by recording fluorescence intensity from microparticle array; reduced oxygen levels or the reduced pH in the local gel environment, as indicated by the bead-anchored dyes, serve as an indirect indication of glucose concentration.

Figure 16:
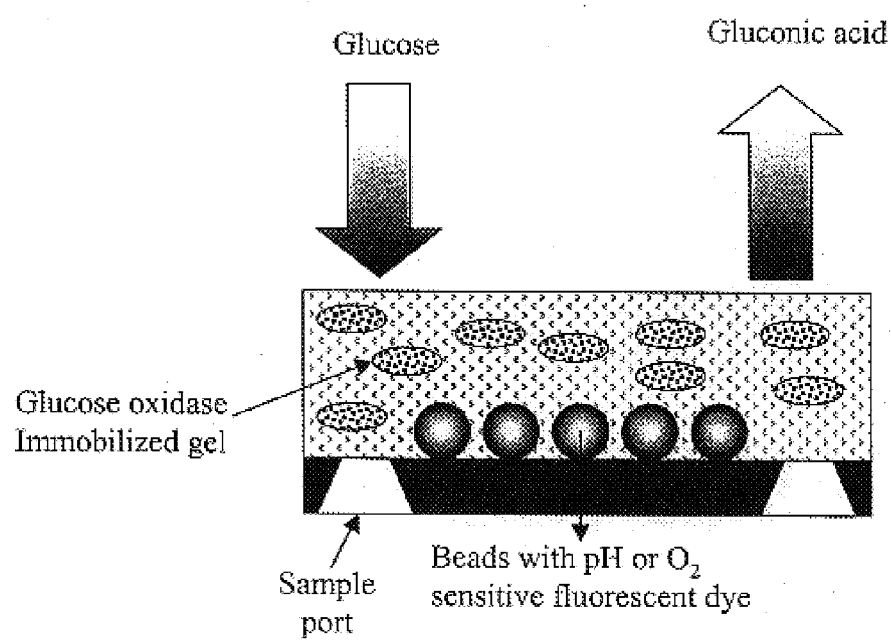
FIG. 16 is an illustration showing a glucose biosensor.

In a preferred embodiment, the silicon electrode contains a set of access ports as illustrated in FIG. 13. In the resulting sensor (FIG. 16) the enzyme glucose-oxidase is immobilized covalently in the gel film, with microparticles functionalized or loaded with pH-sensitive or oxygen-sensitive fluorescent dyes.

Example 11

Gel-Embedded Cellular Arrays and Their Use in Cell-Based Functional Assays

The entrapment and immobilization of viable cells in various polymeric matrices, natural or synthetic, including polyacrylamide (Vorlop, K. et al. Biotechnol. Tech. 6:483 (1992)) have been reported, primarily in connection with biocatalysis (Willaert, P. G. et al. (Eds.), "Immobilized living cell systems: Modeling and experimental methods." Wiley, New York, 1996). Polymeric matrices can provide a hydrated environment containing nutrients and cofactors needed for cellular activity and growth. To minimize mass transfer limitations, methods of the present invention may be used to immobilize arrays of cells in a thin and porous gel film.

In accordance with the methods of the present invention, the process of forming a composite structure containing cell arrays entrapped in a patterned or monolithic gel film consists of two stages. First, ordered cell arrays are formed from a cell suspension also containing all ingredients required for subsequent in-situ gel formation in accordance with Example 1. In a preferred embodiment of the array assembly process, LEAPS (Example 1) is invoked to form arrays from cells suspended in a low viscosity dispersion of monomer(s) mixed with an initiator in accordance with Example 1. Second, gels films are formed, either via heat-initiated in-situ polymerization to form a spatially patterned composite or via UV-initiated in-situ polymerization to form a monolithic composite, as described in Example 2.

The immobilized cell array system of this invention is useful for a variety of assay formats. For example, to analyze and quantify several molecular targets within a sample substance, the methods of this invention provide means to form a gel-embedded cell array displaying a plurality of receptors (to one or more of the targets) which may be exposed to the sample substance.

Figure 18:
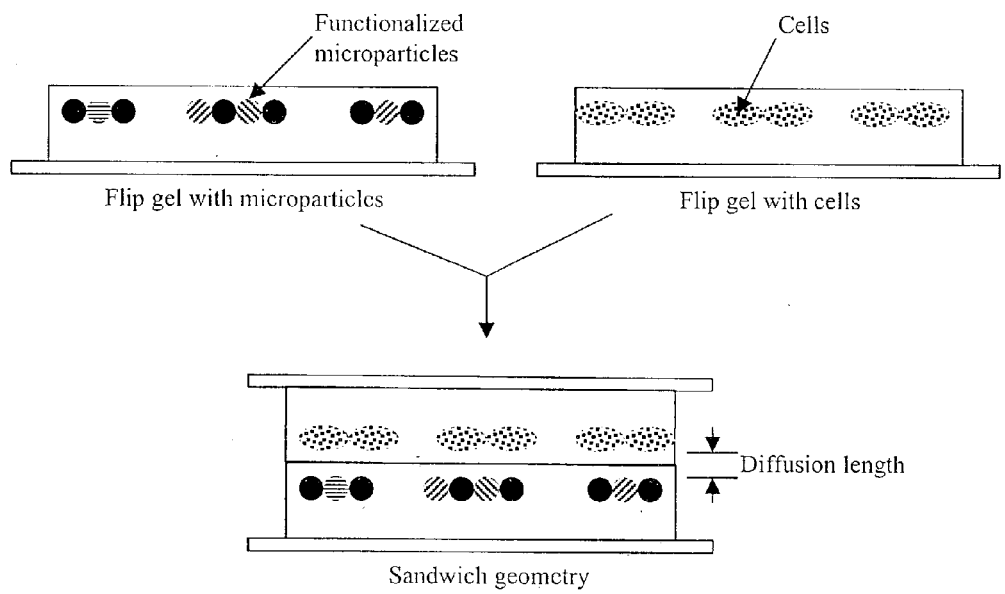
FIG. 18 is an illustration showing a gel-embedded cellular array and its use.
Figure 18:
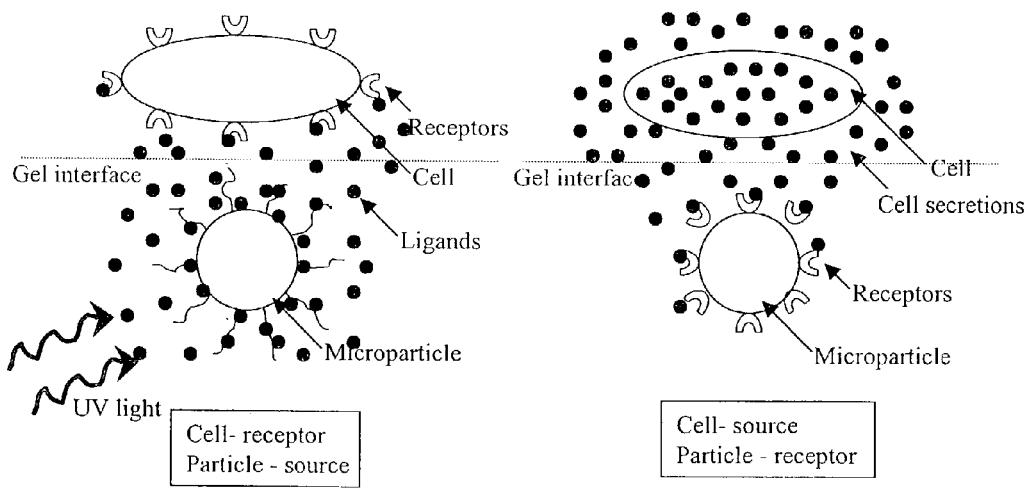

An alternative format of a functional assay, shown in FIG. 18, involves the combination of a gel-microparticle heterostructure with a gel-embedded cellular array prepared by the methods of this invention. Embedding cells within a thin gel film facilitates the engineering of small, functionally organized heterostructures by avoiding the manipulation of individual cells while providing local chemistries capable of maintaining cells in their requisite environment. The lateral spacing of cells as well as microparticles within their respective arrays is readily tuned in such a structure using LEAPS as disclosed herein.

In an embodiment of this invention, two separate gel films, one containing a functionalized microparticle array and the other a cellular array, are placed in direct contact in a sandwich geometry. In this configuration, particles and cells form pairs of sources and detectors of molecules to be analyzed. For example, cells can secrete molecules such as cytokines, and proximal beads within the bead array can be designed to monitor the profile, for example in a displacement assay. Alternatively, small molecules can be photo-chemically cleaved from an array of color-encoded beads and can be detected by monitoring the functional response of cells within the apposed gel-embedded array. The lateral patterning of the arrays as well as the short diffusion length in the vertical direction helps to prevent lateral mixing of the ligand molecules and hence enables execution and monitoring of complex local binding chemistries.

Example 12

Characterization and Control of Diffusive Transport in Gels

Figure 19:
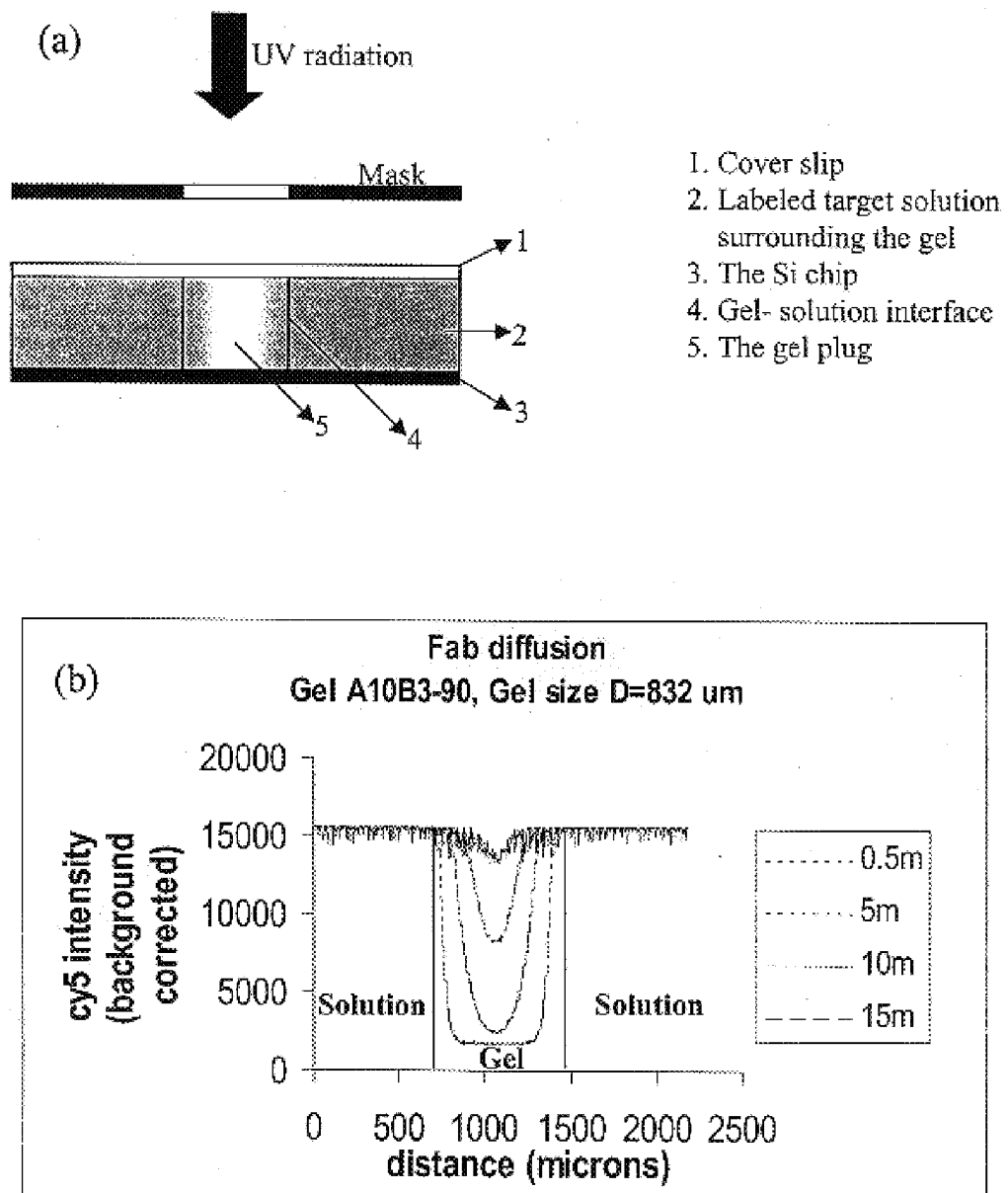
FIG. 19 shows the effect of gel chemistry and formation conditions on diffusion.

The diffusion of fluorescently tagged molecules into the gels of the present invention were studied using a sandwich cell device as illustrated in FIG. 19a. To provide actual chemical anchoring of the gel to both the Si-chip surface and the glass coverslip both of them were pretreated using vinylmethoxysiloxane oligomer for polyacrylamide gels, and 3-(glycidoxypropyl)-trimethoxysilane for agarose gel, respectively.

For the coating reaction a 95% ethanol and 5% water solution was adjusted to pH 5 with acetic acid. The silane coupling agent was then added to yield a 2 wt % solution. Substrates (chips and cover glasses) were dipped into the solution with gentle agitation for 5 minutes. Following, the substrates were removed from the solution and rinsed briefly in ethanol. The treated substrates were cured at room temperature for 24 hours.

For the formation of the acrylamide gels the monomer mixture of 10% (w/v) acrylamide, 3% (w/v) NN'-methylene-bis-arylamide (Polysciences, Ltd, USA), 0.1% photo initiator 1-[4-2-Hydroxyethoxy)-phenyl]2-hydroxy-2-methyl-1-propane-1-one (IRGACURE® 2959, Ciba Specialty Chemicals (USA)) as well as H$_2$O was injected into the sandwich cell. The masked cell was then exposed to a UV light source (150 W Hg lamp) through a photo-mask for durations ranging from 45 s to 180 s. Following the exposure, the unpolymerized solution was removed from the cell.

For agarose gel formation, one microliter of an agarose solution (0.5% w/v) (heated to ~90° C.) was carefully added to the surface of a pretreated Si chip by pipette, and gently covered with a pretreated cover glass slide. Under these conditions the drop of the agarose sol deformed into an approximately cylindrical plug sandwiched between the two surfaces, and turned into a gel under room temperature condition within 1–2 minutes. Once formed, the gel was left undisturbed at room temperature for additional 2–3 hours to promote covalent crosslinking between the hydroxyl groups in the agarose chains and the epoxy group present on the pretreated surfaces.

Example 13

Polymer-Microparticle Composites Using a Thermally Reversible Gel

Figure 20A:
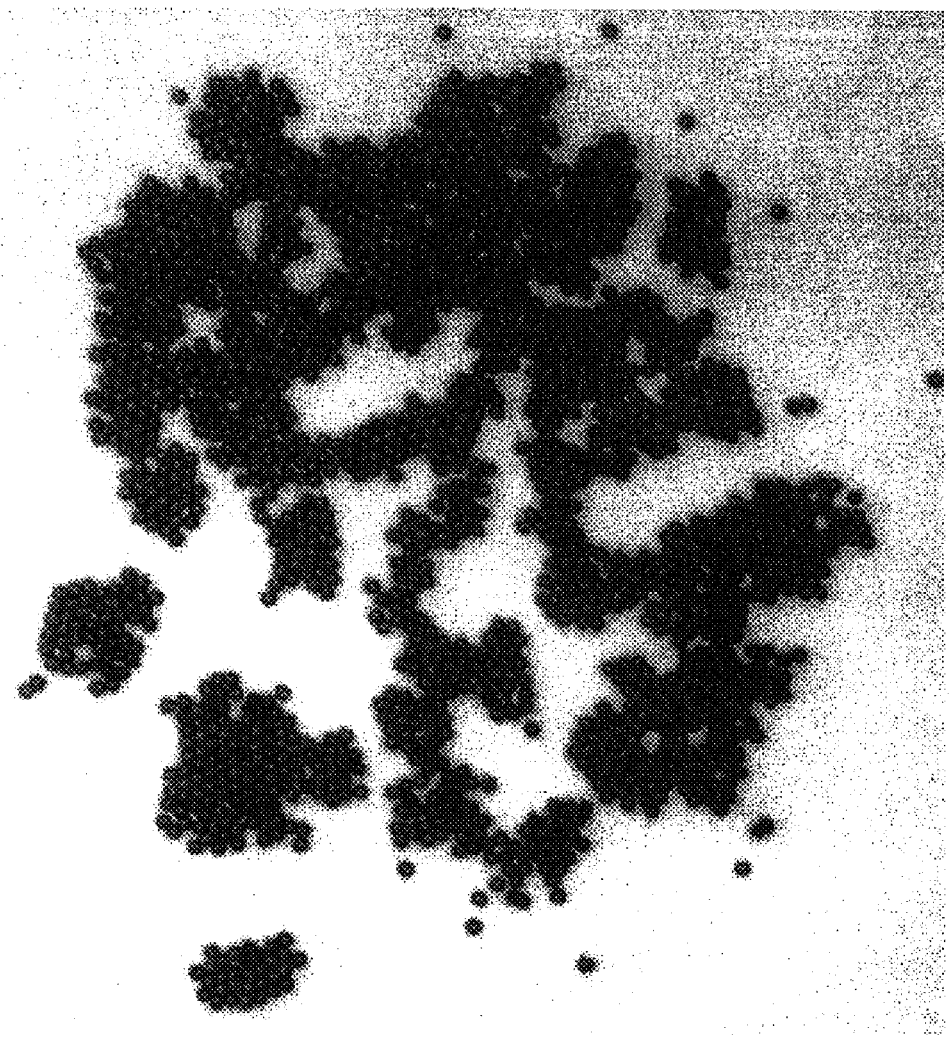
FIG. 20a is a photograph showing the close up of a microparticle array in a gel-microparticle composite film created by using agarose as the gel matrix and 2.8 micron Oligo(dT)$_{25}$ particles. The thickness of the film was ~100 microns.

The microparticles were assembled in a 0.5% to 0.15% Ultrapure Agarose solution (Melting temperature~65° C., Sigma-Aldrich, St. Louis, Mo.), using a temperature-controlled sandwich cell maintained at ~55° C. The method of assembly was as described in the earlier examples. After the array assembly was complete (1–3 minutes), the heater was switched off and the whole assembly was cooled down rapidly to about 5° C. using a cold air gun. This cooling induced the formation of an agarose gel. The microparticle arrays that were embedded in the agarose gel (FIG. 20a) were further used in hybridization-based assays as described below.

Figure 20B:
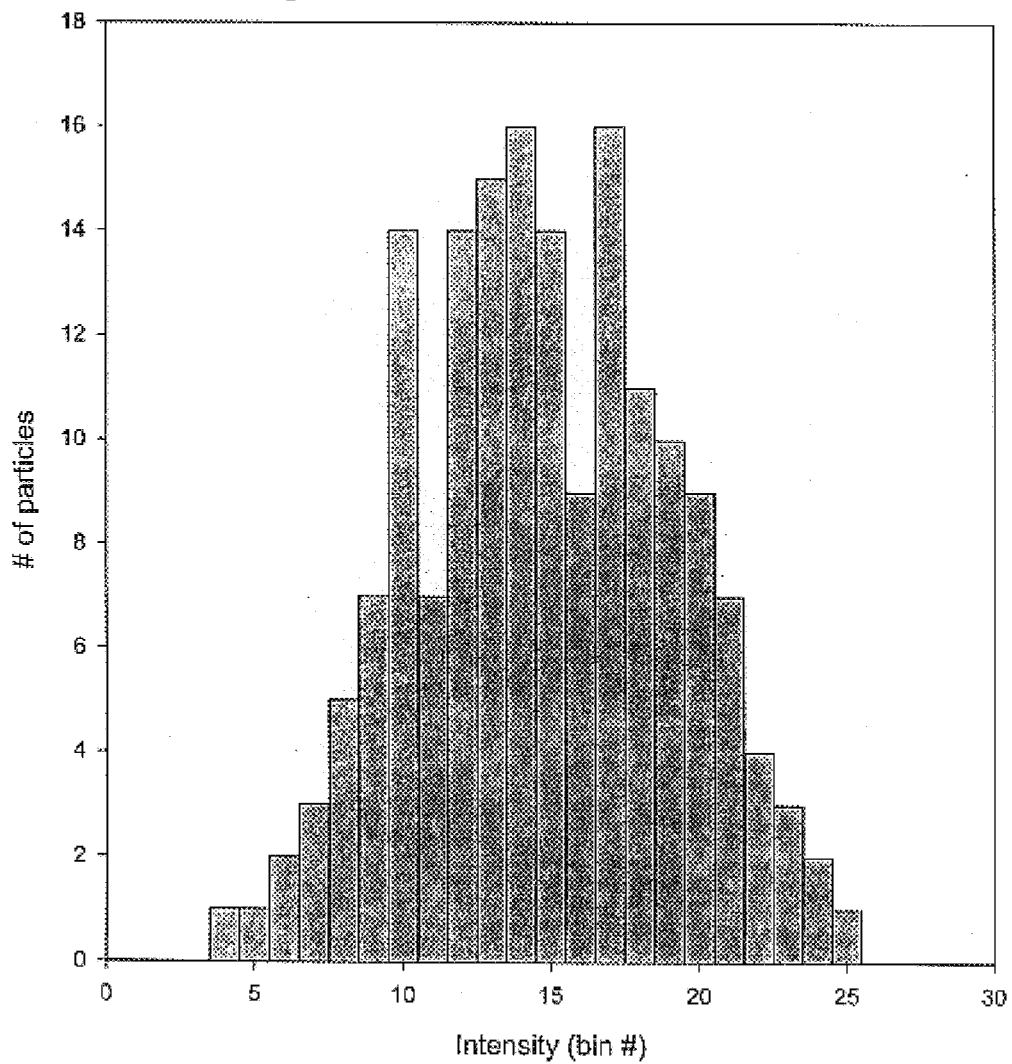
FIG. 20b is an illustration showing the results of a hybridization assay using the 2.8 micron Oligo(dT)$_{25}$ particles. The target was a fluorescently labeled 100 bp synthetic DNA fragment with a complementary poly(A) tail. The thickness of the film was approximately 100 microns.

Oligo(dT)$_{25}$-coupled magnetic particles (2.8 µm, Dynal, Norway) were used to create agarose gel embedded microparticle arrays in a sandwich cell as described above. The sample (20 µl of hybridization mixture containing Cy5-labeled 100 bp-long complementary target, 50 µM) was applied to the film and incubated at 55° C. for 30 minutes. Following the reaction, the film was washed once with TMAC and the light intensity distribution of the microparticles in the gel was analyzed (see Example 7). The resulting histogram and data are shown in FIG. 20b.

Figure 20C:
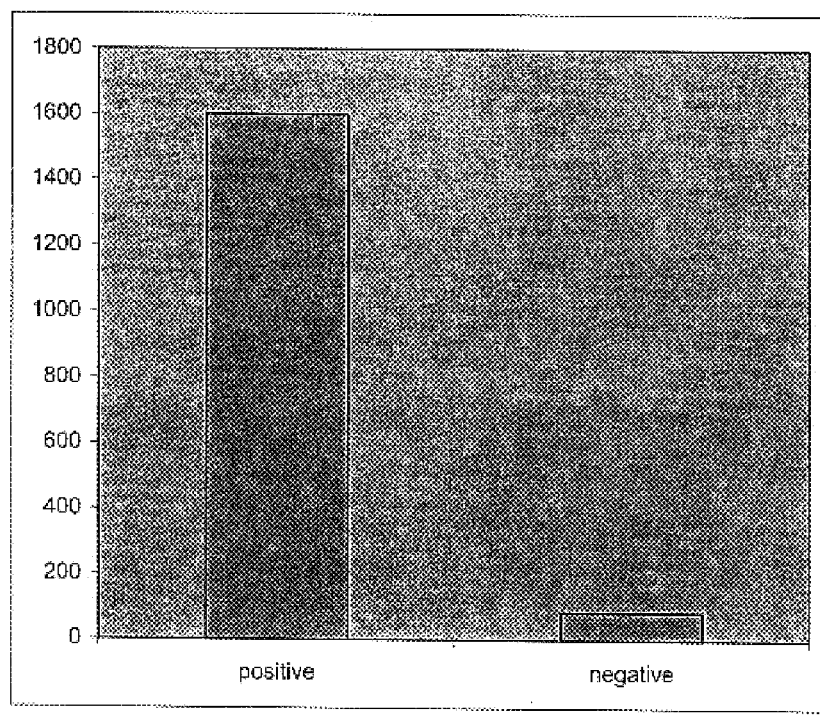
FIG. 20c is an illustration showing the results of an enzymatic extension based hybridization assay using a gel-microparticle composite film consisting of two populations of particles: one with a matching (positive) oligonucleotide probe and the other with a nonmatching (negative) oligo-nucleotide probe. The target was a fluorescently labeled PCR amplified ~280 base pair fragment. The thickness of the film was about 50 microns.

Two different types of Oligo probe-coupled particles (3.2 µm, Bangs Labs, Ind.), (one complementary to a PCR fragment and the other noncomplementary to the target) were used in an extension-based hybridization assay using a FlipGel format. An aliquot of 10 µl of a 100 nM solution of the target (280 bp PCR fragment) in annealing buffer of 0.2 M NaCl, 0.1% Triton X-100, 10 mM Tris/pH 8.0, 0.1 mM EDTA was applied to the gel and allowed to react for 15 min at 30° C. The gel was then washed once with the same buffer and was then covered with an extension reaction mixture that comprised the following: 100 nM of TAMRA-ddCTP (absorption/emission: 550/580 nm) (PerkinElmer Bioscience, Boston, Mass.), and 10 µM dATP-dGTP-dTTP, ThermoSequenase (Amersham, Piscataway, N.J.) in the associated buffer supplied by the manufacturer. The reaction was allowed to proceed for 5 min at 60° C., and the chip was then washed in H$_2$O. Decoding and assay images of the chip were acquired as described before (Example 7). The results are shown in FIG. 20c.

Although a few exemplary embodiments of this invention have been described in detail above, those skilled in the art will appreciate that many modifications of the preferred embodiments are possible using the novel teachings and advantages of this invention. Accordingly all such modifications are intended to be included within the scope of this invention, as defined in the following claims.

We claim:

1. A method of detecting a binding interaction between a biomolecule and a compound, comprising:
   (A)(i) providing a device having a first electrode in a first plane and a second electrode in a second plane;
   (ii) providing a polymerization composition between said first and second electrodes wherein different types of beads are suspended in said polymerization composition, said different types of beads having different biomolecules attached thereto; and wherein the different types of beads are distinguishable by a unique chemical or physical characteristic that identifies said bead type;
   (iii) generating an AC electric field with said first electrode such that the beads are moved to form one or more primary arrays of different types of beads;
   (iv) polymerizing said polymerization composition to form a first polymeric film, wherein said primary arrays of different types of beads are embedded in said first polymeric film;
   (v) removing said first polymeric film from said first electrode;
   (B)(i) providing a polymerization composition on said first electrode, wherein cells secreting said compound are suspended in said polymerization composition;
   (ii) generating an AC electric field with said first electrode such that the cells are moved to form one or more secondary arrays of cells; (iii) polymerizing said polymerization composition to form a second polymeric film, wherein said secondary arrays of cells are embedded in said second polymeric film;
   (iv) removing said second polymeric film from said first electrode; and
   (C) contacting said first polymeric film with said second polymeric film, thereby allowing said compound secreted by said cells to diffuse from said second polymeric film to said first polymeric film and to bind to a corresponding biomolecule to form a compound-biomolecule complex; and
   detecting the compound-biomolecule complex by identifying the unique chemical or physical characteristic of the bead to which the biomolecule that binds to the compound is attached.

2. The method of claim 1 wherein the biomolecules are ligands.

3. The method of claim 1 wherein the biomolecules are oligonucleotides, nucleic acid fragments, or proteins.

4. The method of claim 3, wherein the nucleic acid fragments are DNA fragments.

5. The method of claim 3, wherein the proteins are antibodies or oligopeptides.

6. The method of claim 1 wherein the unique chemical or physical characteristic is color.

7. The method of claim 6 wherein the color is provided by a fluorophore or chromophore dye.

8. The method of claim 1 wherein the target compound is a ligand.

9. The method of claim 8 wherein the compound is an oligonucleotide, a nucleic acid fragment, or a protein.

10. The method of claim 9, wherein the nucleic acid fragment is a DNA fragment.

11. The method of claim 9, wherein the protein is an antibody or an oligopeptide.

12. The method of claim 1 wherein said polymeric films are covalently attached to one of said electrodes.

13. The method of claim 12 wherein said covalent attachment is facilitated by coating one of said electrodes with vinyl siloxane.

14. The method of claim 1 wherein said polymerization composition comprises a monomer, an initiator, and a cross-linker in solution.

15. The method of claim 14 wherein said initiator is a photoinitiator, and wherein the method further includes exposing said composition to UV light to initiate polymerization.

16. The method of claim 14 wherein said initiator is a thermal initiator, and wherein the method further includes heating said composition to initiate polymerization.

* * * * *